US006217826B1

(12) United States Patent
Reeder et al.

(10) Patent No.: US 6,217,826 B1
(45) Date of Patent: Apr. 17, 2001

(54) MEMBRANE APPARATUS WITH ENHANCED MASS TRANSFER, HEAT TRANSFER AND PUMPING CAPABILITIES VIA ACTIVE MIXING

(75) Inventors: Gary D. Reeder, Beulah, CO (US); Mark J. Gartner, Wexford, PA (US); Harvey S. Borovetz; Philip Litwak, both of Pittsburgh, PA (US)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/157,815

(22) Filed: Sep. 21, 1998

Related U.S. Application Data

(63) Continuation-in-part of application No. 08/837,048, filed on Apr. 11, 1997, now Pat. No. 6,106,776.

(51) Int. Cl.[7] .............................. A61M 1/14; A61M 1/34; A61M 1/36; A61M 37/00; B01D 24/28

(52) U.S. Cl. ........................ 422/45; 604/4.01; 604/6.13; 604/6.14; 422/48; 422/44; 210/780

(58) Field of Search ................................... 604/4–8, 4.01, 604/5.01, 6.09, 6.1, 6.11, 6.13, 6.14; 422/44–46, 48; 210/767, 780–82, 784, 649–50

(56) References Cited

U.S. PATENT DOCUMENTS

| | | | |
|---|---|---|---|
| 3,026,871 | 3/1962 | Thomas | 128/214 |
| 3,291,568 | * 12/1966 | Sautter . | |
| 3,332,746 | 7/1967 | Claff et al. | 23/258.5 |
| 3,352,422 | * 11/1967 | Heden . | |
| 3,396,849 | 8/1968 | Lande et al. | 210/321 |
| 3,480,401 | 11/1969 | Holm et al. | 23/258.5 |
| 3,579,810 | 5/1971 | Mon | 29/527.1 |

(List continued on next page.)

OTHER PUBLICATIONS

Lawyers"Medical Cyclopedia, "I. The Thorax and Respiratory System", §33.1 –§33.10, Need Date, 4–15.
"Resonance Energies–Respiration, Respiratory System", 215–226.
Extracororeal Medical Specialities, Inc. (EMSI), Interpulse [TM] Membrane Oxygenation System, Instructions for Use, 1981, 1–18 (plus 2 sheets of drawing).
Makarewicz, A. J. et al., "A Dynamic Intravascular Artificial Lung", *ASAIO J.*, 1994, M747–M750.
Makarewicz, A. J. et al., "A Pumping Artificial Lung", *ASAIO J.*, 1994, M518–M521.
Nose Y. (ed.), "The Oxygenator", *Manual on Artificial Organs*, The C. V. Mosby Company, Saint Louis, 1973, vol. II, pp. 1–2, 4, 6,10, 12–14, 25–38, 127–162, 175–185.
Searle Cardio–Pulmonary Systems, Inc. "Searle Membrane Oxygenator", brochure, 1975, 4 pages.
Thomas, J. A. et al., "A Heart–Lung Machine with Artificial Pulmonary Membrane: First Surgical Results38 , *Arch Mal Coeur*, 1958, 51, 801–811 (English translation included).

(List continued on next page.)

*Primary Examiner*—Angela D. Sykes
*Assistant Examiner*—Patricia Bianco
(74) *Attorney, Agent, or Firm*—Woodcock Washburn Kurtz Mackiewicz & Norris LLP

(57) ABSTRACT

A combination mass transfer and pump apparatus, which in a single step actively mixes a first mass and a second mass and simultaneously pumps one of the first mass and the second mass through the apparatus. The combination mass transfer and pump apparatus substantially comprises a housing and at least one distributor element having a plurality of selectively fluid-permeable membrane elements wherein the at least one distributor element is agitated within the second mass such that the first mass diffuses across the selectively fluid-permeable membrane elements, mixing with the second mass, and in the same step the second mass is pumped through the housing.

42 Claims, 20 Drawing Sheets

U.S. PATENT DOCUMENTS

| | | |
|---|---|---|
| 3,674,440 * | 7/1972 | Kitrilakis . |
| 3,794,468 | 2/1974 | Leonard ................................ 23/258.5 |
| 3,841,837 * | 10/1974 | Kitrilakis et al. . |
| 3,907,504 | 9/1975 | Hammond et al. ................... 23/258.5 |
| 3,927,980 | 12/1975 | Leonard ................................ 23/258.5 |
| 3,998,593 | 12/1976 | Yoshida ........................ 23/258.5 MH |
| 4,033,724 | 7/1977 | Tamiya .......................... 23/258.5 BH |
| 4,151,088 | 4/1979 | Wolf, Jr. et al. ..................... 210/180 |
| 4,158,693 | 6/1979 | Reed et al. .............................. 422/46 |
| 4,163,721 | 8/1979 | Lobdell ................................ 210/232 |
| 4,165,287 | 8/1979 | Goyne .................................. 210/232 |
| 4,179,364 | 12/1979 | Bratten et al. .................... 210/321 B |
| 4,239,625 | 12/1980 | Hlavinka ........................... 210/321.3 |
| 4,312,757 | 1/1982 | Brumfield .................. 210/321.63 X |
| 4,402,420 | 9/1983 | Chernack .............................. 220/266 |
| 4,424,190 | 1/1984 | Mather, III et al. .................... 422/46 |
| 4,455,230 | 6/1984 | Elgas et al. ........................... 210/232 |
| 4,476,685 | 10/1984 | Aid ............................................ 62/3 |
| 4,487,558 | 12/1984 | Troutner ................................ 417/477 |
| 4,490,331 | 12/1984 | Steg, Jr. .................................. 422/46 |
| 4,573,884 | 3/1986 | Troutner ................................ 417/374 |
| 4,574,876 | 3/1986 | Aid .......................................... 165/46 |
| 4,620,965 | 11/1986 | Fukusawa et al. ..................... 422/46 |
| 4,639,353 * | 1/1987 | Takemura et al. ..................... 422/46 |
| 4,659,549 | 4/1987 | Hamada et al. ........................ 422/48 |
| 4,698,207 | 10/1987 | Bringham et al. ..................... 422/46 |
| 4,735,775 | 4/1988 | Leonard et al. ........................ 422/46 |
| 4,766,768 | 8/1988 | Norling .................................... 73/497 |
| 4,818,490 | 4/1989 | Carson et al. .......................... 422/46 |
| 4,876,066 | 10/1989 | Bringham et al. ..................... 422/46 |
| 4,902,476 | 2/1990 | Gordon et al. ......................... 422/46 |
| 4,911,846 | 3/1990 | Akasu et al. .......................... 210/645 |
| 4,975,247 | 12/1990 | Badolato et al. ....................... 422/48 |
| 5,002,890 | 3/1991 | Morrison .............................. 435/286 |
| 5,011,469 | 4/1991 | Buckberg et al. ........................ 604/4 |
| 5,034,135 | 7/1991 | Fischel ................................. 210/651 |
| 5,037,383 | 8/1991 | Vaslef et al. ........................... 604/26 |
| 5,143,630 | 9/1992 | Rolchigo ............................... 210/780 |
| 5,236,665 | 8/1993 | Mathewson et al. ................... 422/46 |
| 5,263,924 | 11/1993 | Mathewson ............................. 604/4 |
| 5,270,005 | 12/1993 | Raible .................................... 422/46 |
| 5,271,743 | 12/1993 | Hattler ................................... 604/26 |
| 5,311,932 | 5/1994 | Sen et al. .......................... 165/109.1 |
| 5,312,589 | 5/1994 | Reeder et al. .......................... 422/45 |
| 5,316,724 * | 5/1994 | Mathewson et al. ................... 422/48 |
| 5,358,689 * | 10/1994 | Jones et al. ............................. 422/46 |
| 5,411,706 * | 5/1995 | Hubbard et al. ........................ 422/46 |
| 5,578,267 | 11/1996 | Cosentino et al. ..................... 422/46 |
| 5,626,819 * | 5/1997 | Novello et al. ......................... 422/45 |
| 5,668,329 | 9/1997 | Petri ................................... 73/862.59 |
| 5,770,149 * | 6/1998 | Raible .................................... 422/46 |
| 5,817,278 | 10/1998 | Fini et al. ............................... 422/45 |
| 5,823,987 * | 10/1998 | Elgas et al. ............................... 604/4 |
| 5,830,370 * | 11/1998 | Maloney, Jr. et al. ............... 210/780 |
| 5,900,142 | 5/1999 | Maloney, Jr. et al. ............... 210/179 |

OTHER PUBLICATIONS

Levich, "Diffusion Rates in Turbulent Flow", Ch. III, 139–184 and "Heat Transfer in Fluids", Ch. VI, 185–206 in *Physiochemical Hydrodynamics*, Prentice Hall, Englewood Cliffs, N.J., 1962 (English translation from Russian).

Schlichting, "Origin of Turbulence II", Ch. XVII, 489–554, in *Boundary Layer Theory*, McGraw Hill, New York, 1962 (English translation from Russian).

* cited by examiner

MEMBRANE APPARATUS WITH ENHANCED MASS TRANSFER, HEAT TRANSFER AND PUMPING CAPABILITIES VIA ACTIVE MIXING

This is a continuation-in-part of U.S. patent application Ser. No. 08/837,048 filed in the United States Patent and Trademark Office on Apr. 11, 1997 now U.S. Pat. No. 6,106,776 which is incorporated by reference in its entirety, herein.

BACKGROUND OF THE INVENTION

1. Field of the Invention

This invention relates to a combination mass transfer and pump apparatus, which in a single step actively mixes a first mass and a second mass and simultaneously pumps one of the first mass and the second mass through the apparatus. More particularly, this invention concerns a combination mass transfer and pump apparatus substantially comprising a housing and at least one distributor element having a plurality of selectively fluid-permeable membrane elements carrying the first mass, wherein the at least one distributor element is agitated within the second mass such that the first mass and/or the second mass diffuse across the plurality of the selectively fluid-permeable membrane elements and in the same step the second mass is pumped through the housing.

2. Description of the Related Art

Mass transfer apparatus can take the form of a membrane oxygenator, which is used to oxygenate blood. Oxygenation of blood is important, for example, in performing surgical procedures, such as open heart surgery, where the heart is stopped and the patient's blood is pumped artificially, requiring oxygenation. One type of conventional membrane oxygenator employs bundles of stationary hollow fibers retained within a cylindrical housing wherein oxygen is pumped through the hollow fibers in the same direction as the blood being pumped through the oxygenator housing. The hollow fibers consist of microporous membranes, which are impermeable to blood and permeable to gas. Gas exchange takes place when venous blood flows through the housing and contacts the hollow fibers. Based on the law of diffusion, oxygen diffuses across the hollow fiber walls and enriches venous blood in contact with these hollow fibers. Examples of this type of membrane oxygenator are described in U.S. Pat. No. 4,620,965 issued to Fukusawa et al. and U.S. Pat. No. 4,698,207 issued to Bringham et al. The disadvantage of this type of membrane oxygenator is that a relatively thick blood boundary layer is formed around the hollow fibers, which retards oxygenation of blood that does not directly contact the hollow fibers.

In order to disrupt the blood boundary layer, another type of conventional membrane oxygenator oxygenates blood by directing blood flow substantially perpendicular or at an angle to the hollow membranes carrying the oxygen. Examples of this type of membrane oxygenator are described in U.S. Pat. No. 4,639,353 issued to Takemura et al., U.S. Pat. No. 3,998,593 issued to Yoshida et al. and U.S. Pat. No. 4,490,331 issued to Steg, Jr. Drawbacks to these designs include the need for a large priming volume and large blood-biomaterial exposure area, and the tendency for the permeability of the hollow membranes to decrease over time, causing the oxygenator to become less efficient.

Yet another type of membrane oxygenator discloses moving a part of the oxygenator in order to provide increased mixing of blood and oxygen. Examples of this type of membrane oxygenator are described in U.S. Pat. Nos. 3,674,440 and 3,841,837 issued to Kitrilakis and Kitrilakis et al., collectively, (the "Kitrilakis Patents") and U.S. Pat. No. 3,026,871 issued to Thomas (the "Thomas Patents"). The Kitrilakis Patents disclose a blood flow path positioned around a rotor, wherein the blood flow path and the oxygen flow path is separated by a non-porous membrane layer through which the blood cannot flow. The blood flow travels substantially parallel to the oxygen flow and rotation of the rotor causing mixing by a shearing effect. A characteristic of this device is the use of structures with a wafer-like membrane to separate the blood from the gas phase. In contrast, a distinguishing characteristic of the current device described herein is the use of hollow fiber membranes that both improve pumping action and significantly increase the amount of surface area available for mass transfer. Although the Kitrilakis oxygenator may provide a degree of mixing of the blood, this type of mixing may lead to destruction of red blood cells. While hollow fiber membranes have been and are currently used to oxygenate blood, the devices in which they are used require a separate blood pump, and existing adult units require approximately 2–3 $m^2$ of surface area from the fibers. In contrast, the present invention requires no separate pump, and as little as 0.5 $m^2$ of surface area from the hollow fiber membranes.

The Thomas Patent discloses rotating a single, cylindrical, semi-permeable membrane containing oxygen in a housing wherein blood contacts and flows over the membrane and oxygenation of the blood occurs across the rotating membrane. Disadvantages of this type of membrane oxygenator are that it too tends to form a blood boundary layer along the surface of the membrane. The diffusion of oxygen and carbon dioxide through this blood boundary layer is poor due to the thickness of the boundary layer. Furthermore, since blood films form along the surface of the membrane cylinder there is no mechanism for creating a cross flow component to disrupt the static boundary layer. Accordingly, the overall oxygen and carbon dioxide transfer of this device is poor and the device requires large priming volumes in order to be properly operated.

Yet another type of blood oxygenator device comprises short microporous fiber layers which are folded, twisted and woven around a hollow shaft that carries the inlet and outlet gas flows. The device is implanted into the vascular system of a patient and rotated to cause mixing of the blood. This type of device is explained in greater detail in "A Dynamic Intravascular Lung," *ASAIO Journal*, 1994. A disadvantage of this type of blood oxygenator is that only limited number of fiber layers can be incorporated into the device. This restriction occurs because anatomical space is limited and results in insufficient oxygenation/decarbonation of blood. Furthermore, the rotation of the device within the blood vessel may destroy the cells lining the blood vessel.

With the exception of the Kitrilakis device, all of the blood oxygenators mentioned above require a separate pump apparatus to propel the blood through the oxygenator. Some blood oxygenators even employ two separate pump apparatus, wherein a venous pump is used to pump venous blood to the oxygenator and an arterial pump is used to pump the oxygenated blood from the oxygenator to the patient's arteries. Examples of this type of pump-oxygenator system are disclosed in U.S. Pat. Nos. 3,907,504 and 3,927,980 issued to Hammond et al. and Leonard, respectively. The major disadvantage of pump-oxygenators that employ a multiple step process to pump and oxygenate the blood is that blood may be damaged. Also, this type of approach requires considerable fluid volume to prime the pumps, which leads to clinical complications, difficulty in patient management, and a bulky construction.

Nowhere in the cited related art is there disclosed a combined mass transfer and ump apparatus which effectively oxygenates and pumps blood in one step to sustain a atient for an extended duration, wherein the apparatus is a compact unit. Therefore, there is a definite need for this combination pump-oxygenator, which provides for effective oxygenation/decarbonation and pumping of blood as disclosed in the present invention.

SUMMARY OF THE INVENTION

Accordingly, the present invention provides an apparatus that simultaneously transfers mass between two fluids and simultaneously pumps one of the two fluids through a housing in a single-step. The apparatus of the present invention substantially comprises a housing defining a fluid path, at least one distributor element having a plurality of selectively fluid-permeable membrane elements carrying a first fluid such that when the at least one distributor element is agitated within the housing, active mixing of the first and the second fluids occurs, as well as simultaneous pumping of the second fluid through the housing.

Preferably, the distributor element has an inner ring and an outer ring that are concentrically spaced with respect to one another such that they define a fluid supply plenum and a fluid return plenum. The distributor element further includes a fluid return spoke and a fluid supply spoke that are in fluid communication with the fluid return plenum and the fluid supply plenum, respectively.

The present invention optionally provides for a plurality of distributor elements thus, providing additional selectively fluid-permeable membrane elements and increased surface area at which oxygenation/decarbonation of the blood takes place. The specific number of distributor elements is dependent upon the amount of surface area necessary for the specific patient. For example, a larger patient requires greater oxygen delivery and thus, more surface area where the oxygenation/decarbonation takes place, however, less surface area is necessary for a smaller patient. Further, the present invention provides for the surface area of the selectively fluid-permeable membrane elements to be increased by increasing the number of selectively fluid-permeable membrane elements on each distributor element. Also, selectively fluid-permeable membrane elements can cover both the first face and/or second face of each of the distributor disk. A plurality of layers of the selectively fluid-permeable membrane can cover the first face and /or second face of the distributor elements.

The present invention provides for the selectively fluid-permeable membrane elements to be substantially perpendicular to the bulk fluid flow of the first fluid such that there will be cross flow.

The present invention provides for the selectively fluid-permeable membrane elements to be permeable to gas and impermeable to liquids, such as whole blood when the present invention is used in a blood oxygenator. The blood pump-oxygenator of the present invention provides for the plurality of selectively fluid-permeable membrane elements to be microporous such that the fibers are selectively permeable to the desired fluids. The present invention further provides for the opportunity of the surfaces of the selectively fluid-permeable membrane elements to be coated with a material, which would decrease the tendency for performance degradation over time. An example of the type of material used for these purposes is silicone rubber, although numerous other polymer coatings could be used. However, if the present invention is utilized solely for its pumping capabilities, the rotating disk is preferably porous, but made of material that but for the porous design, is otherwise impermeable to fluids.

In addition to continuous rotation, the present invention further provides for the plurality of rotors being rotated in a back and forth motion such that the rotors repeatedly rotate approximately 360 degrees or less, and then reverse direction, resulting in the blood being agitated via the relative motion of the disk to the blood and the blood boundary layer being disrupted. If the forward and back rotation angles differ, pumping may be affected through an absolute precession of the rotor.

The present invention provides an alternative embodiment, which can be used, solely for pumping blood. This alternative embodiment would substantially comprise a housing defining a fluid path, a rotor, at least one rotor hub on which is mounted the rotor and defining a fluid path and preferably having the selectively fluid-permeable membranes taking the form of a plurality of porous fibers attached to the rotor.

An alternative embodiment would utilize additional layers of fluid-impermeable membrane elements to provide a heat exchanger function. Such layers of additional fluid impermeable membrane elements could be interspersed within the mass exchange layers or constitute a separate thermal regulation member. Alternatively, mass exchange fibers can be positioned on only one side of the distributor element and heat exchange fibers on the other forming another type of integrated heat exchanger.

The present invention further provides an embodiment that can be used for mass transfer. For example, if baffles are positioned adjacent to the distributor elements the intrinsic pumping capability of the present invention will be decreased and an additional pumping element may be required.

The present invention further provides for a method of simultaneous mass transfer and pumping.

The present invention provides a blood pump-oxygenator that can be used to treat patients having acute as well as chronic lung diseases.

The present invention further provides a method of cardiopulmonary bypass support that can be used to support the cardiac surgical patient.

The present invention further may optionally be employed with the use of a "smart control" system to provide an automated control of the principal portions of the cardiopulmonary bypass circuit.

The present invention further provides a method of renal dialysis to treat the blood of patients who suffer from some form of kidney dysfunction.

The present invention further provides a method of liver assist that can be used to treat the blood of patients suffering from hepatic deficiencies.

Other details, objects and advantages of the present invention will become more apparent with the following description of the present invention.

BRIEF DESCRIPTION OF THE DRAWINGS

The accompanying drawings describe the present invention in which.

DETAILED DESCRIPTION OF THE PRESENT INVENTION

Figure 1:
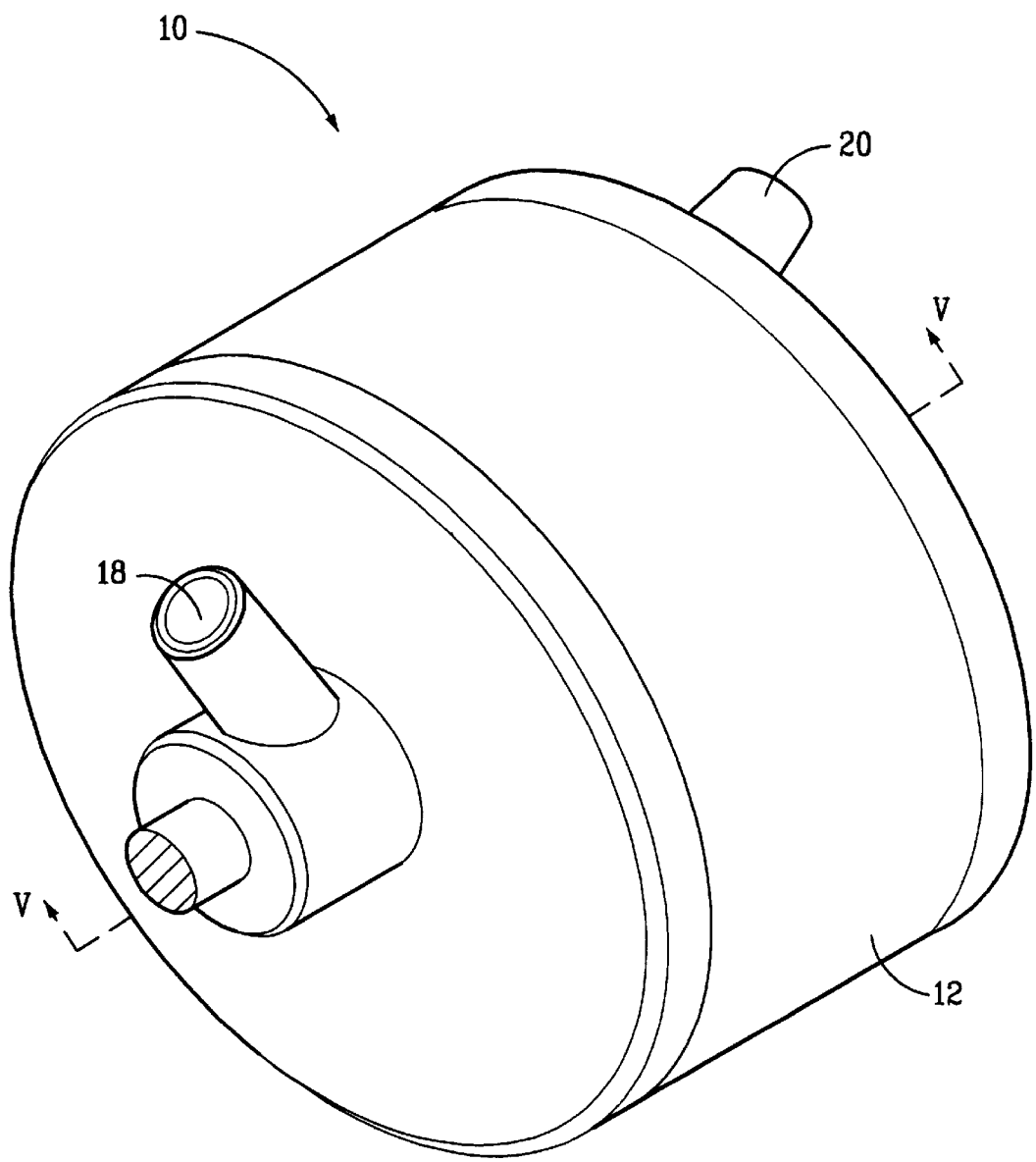
FIG. 1 is a perspective view of an embodiment of the present invention blood membrane oxygenator illustrating the venous blood inlet and arterial blood outlet.
Figure 2:
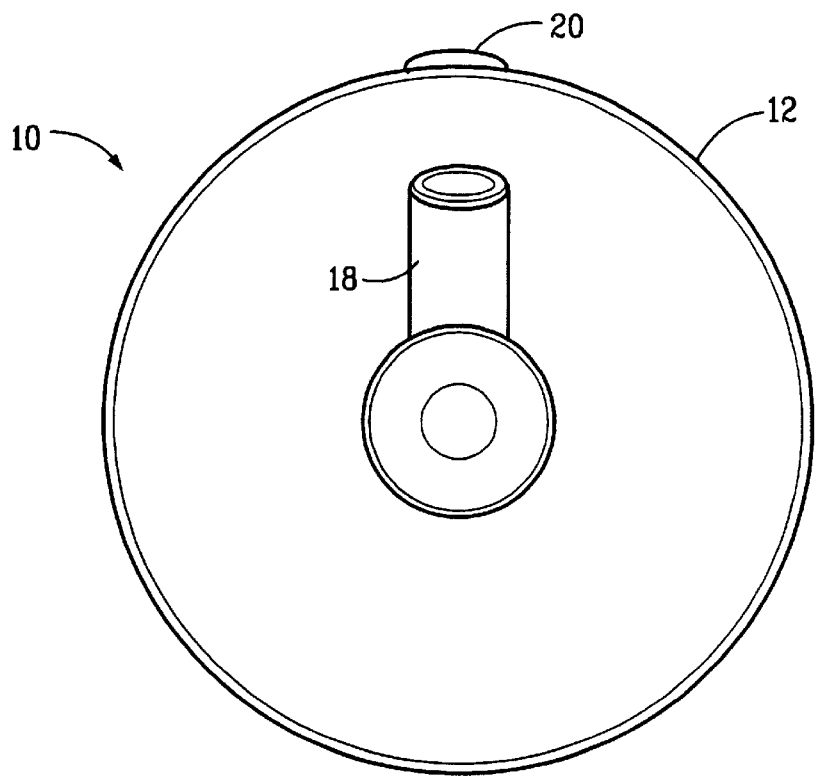
FIG. 2 is a front plan view of the blood membrane oxygenator shown in FIG. 1 illustrating the venous blood inlet.
Figure 3:
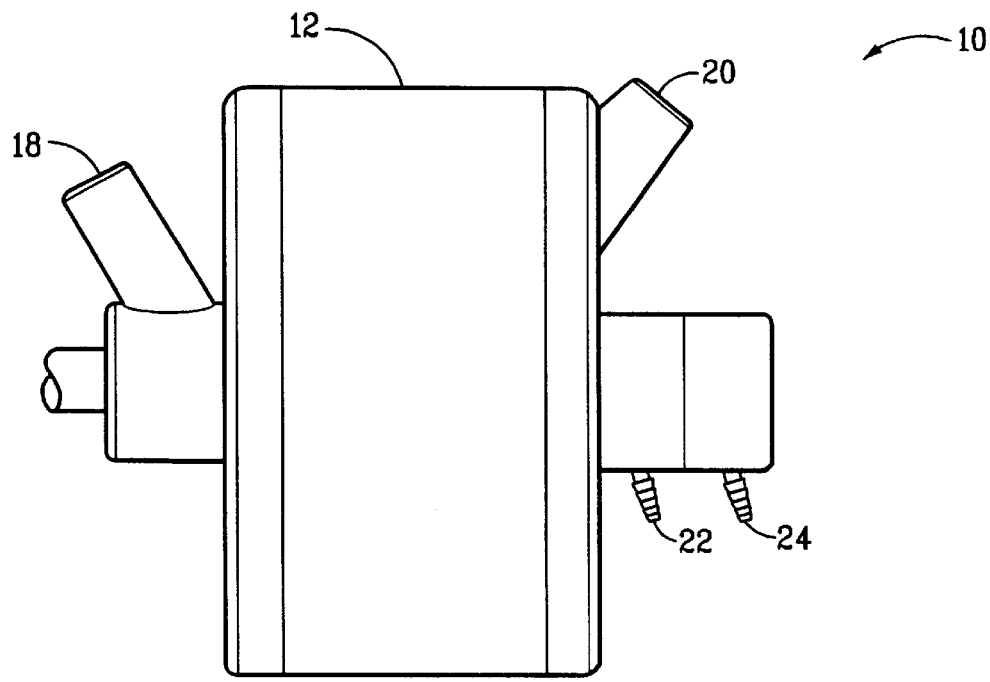
FIG. 3 is a side plan view of the blood membrane oxygenator shown in FIG. 1 further illustrating an oxygen inlet and an oxygen outlet.
Figure 4:
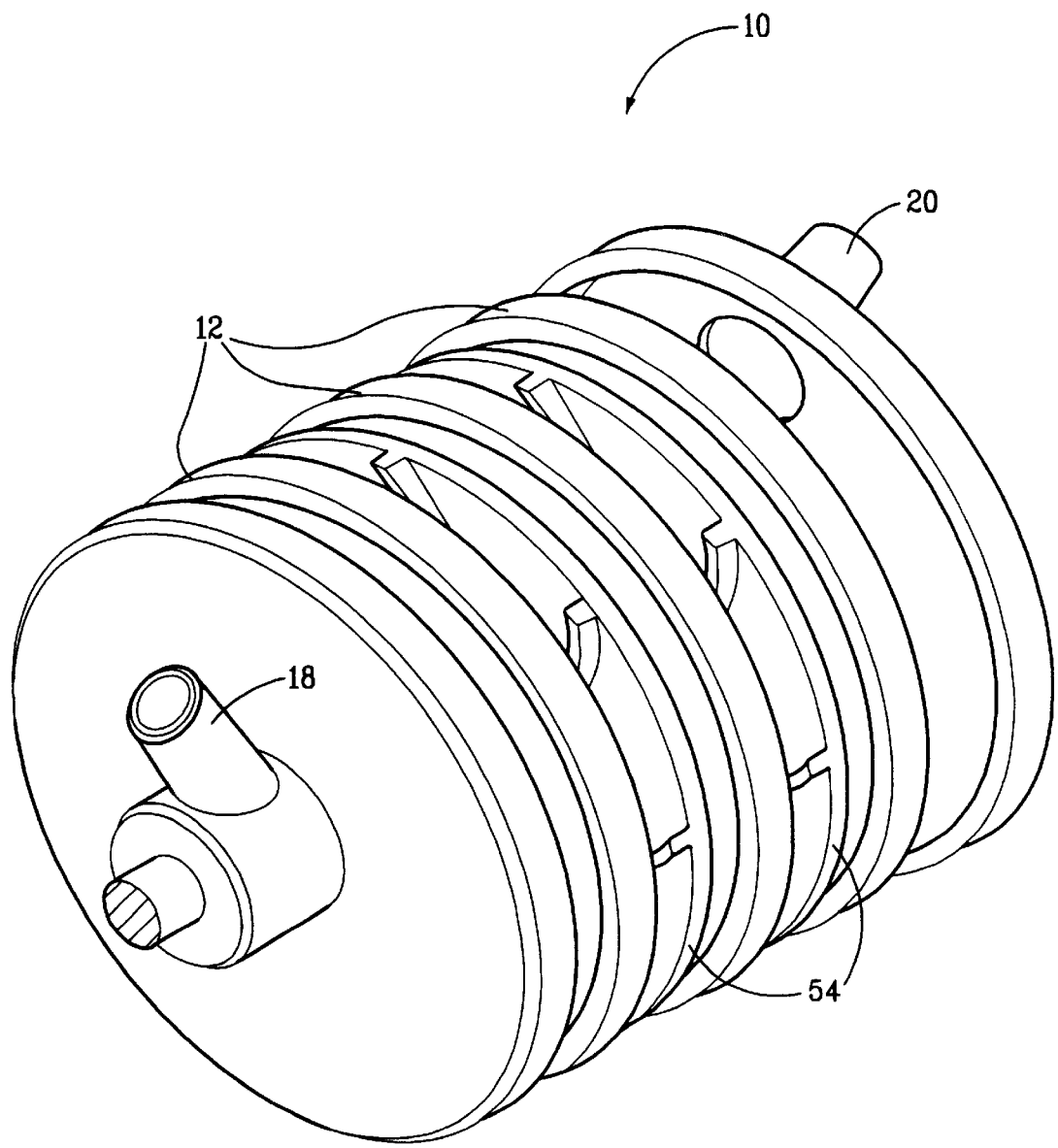
FIG. 4 is a cutaway perspective view of the blood membrane oxygenator shown in FIG. 1 with portions of the cylindrical section of the housing and the rotors eliminated in order to more clearly illustrate baffles of a preferred embodiment.

Although this invention is suitable for other uses it will be described as being used as a combined blood pump-oxygenator to support a patient. Such description is for purposes of explanation and is not intended to limit the scope of this invention. For example, the present invention can also be used as a kidney dialysis machine, a liver assist apparatus, a blood pump and a heat exchanger.

FIGS. 1–5 illustrate a present preferred embodiment of a blood oxygenator 10 comprising a housing 12 defining a blood flow path 13, a rotor hub in the form of a double lumen shaft 14, and a plurality of rotors each comprising hollow fiber distributor disks 16. The housing 12 encases the rotor hub 14 and the hollow fiber distributor disks 16. The housing has a venous blood inlet 18, an arterial blood outlet 20, an oxygen supply inlet 22 and a gas outlet 24 and is preferably made from a biocompatible material such as polycarbonate. Within the housing 12 are a gas inlet chamber 25 and a gas outlet chamber 27. The double lumen shaft defines an oxygen inlet path 29 and a gas outlet path 31 as shown in FIG. 5A. The oxygen inlet path 29 is in fluid communication with the oxygen supply inlet 22 and the gas outlet path 31 is in fluid communication with gas outlet 24. The blood flow path 13, oxygen inlet path 22, and gas outlet path 24 are isolated from one another through seals 15, which may comprise O-rings or lip seals interfacing with the shaft 14.

Figure 8:
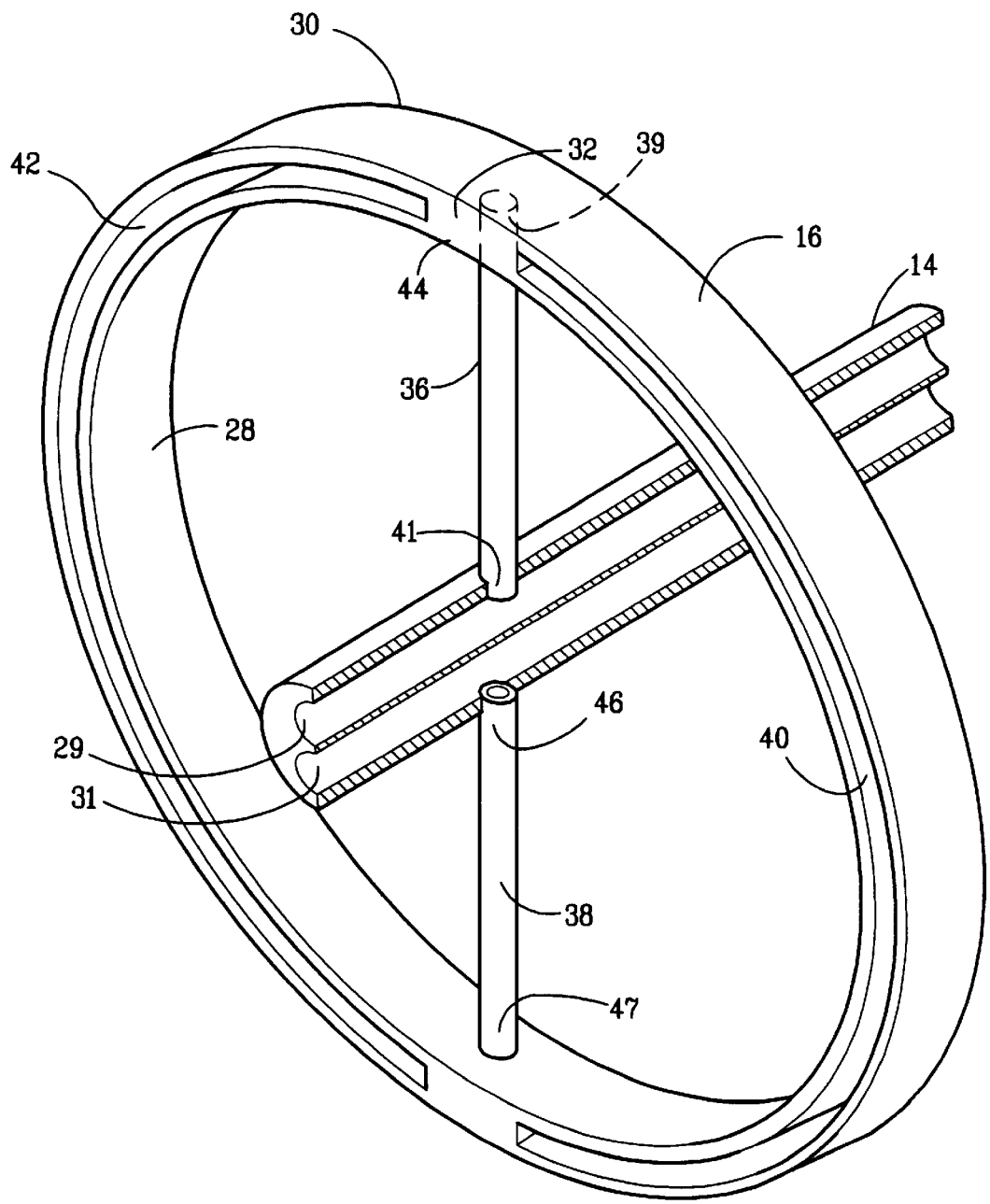
FIG. 8 is a perspective view of one of the distributor disks shown in FIG. 6 with the selectively fluid-permeable membrane elements eliminated therefrom to more clearly illustrate the cross section of the double lumen shaft.
Figure 9:
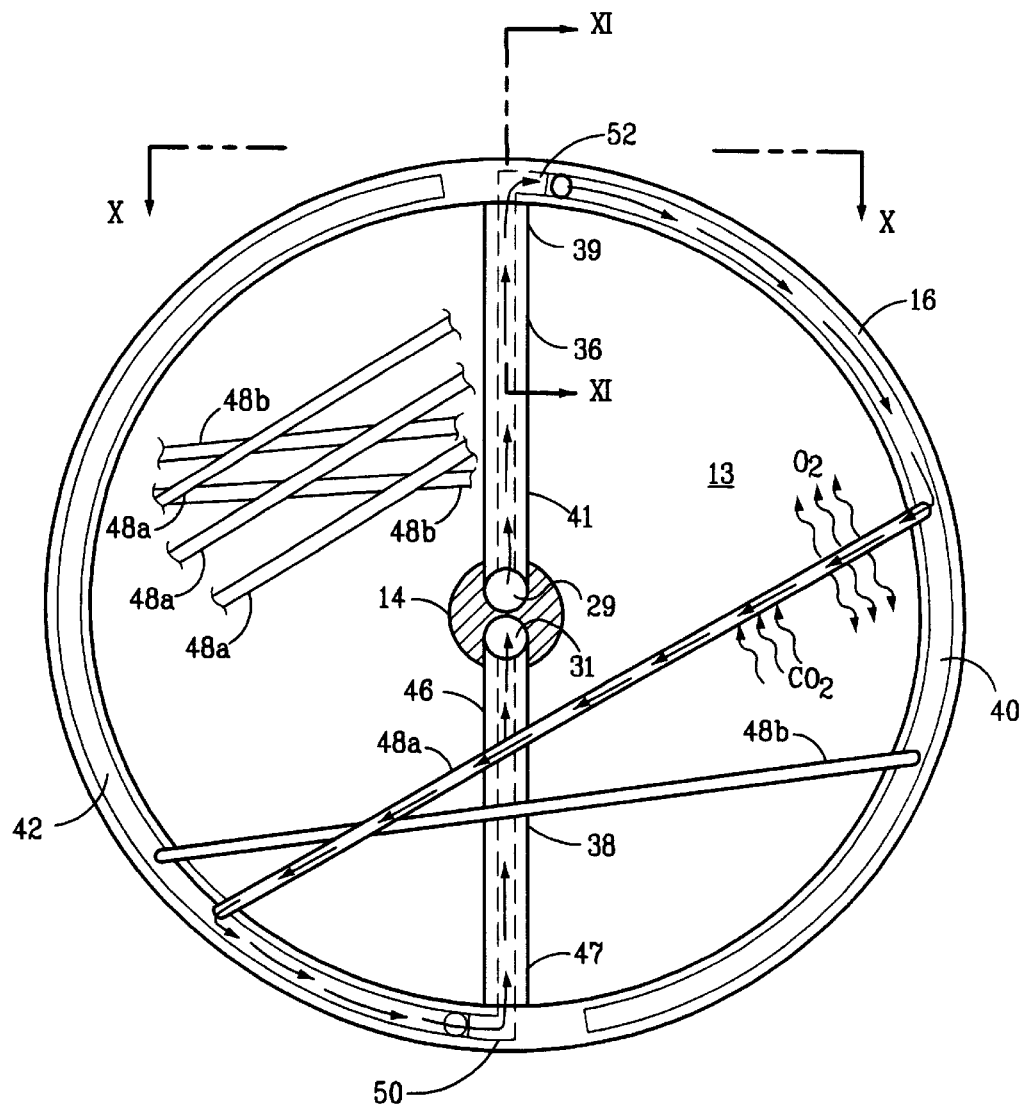
FIG. 9 is a side plan view of the distributor disk shown in FIG. 8.
Figure 10:
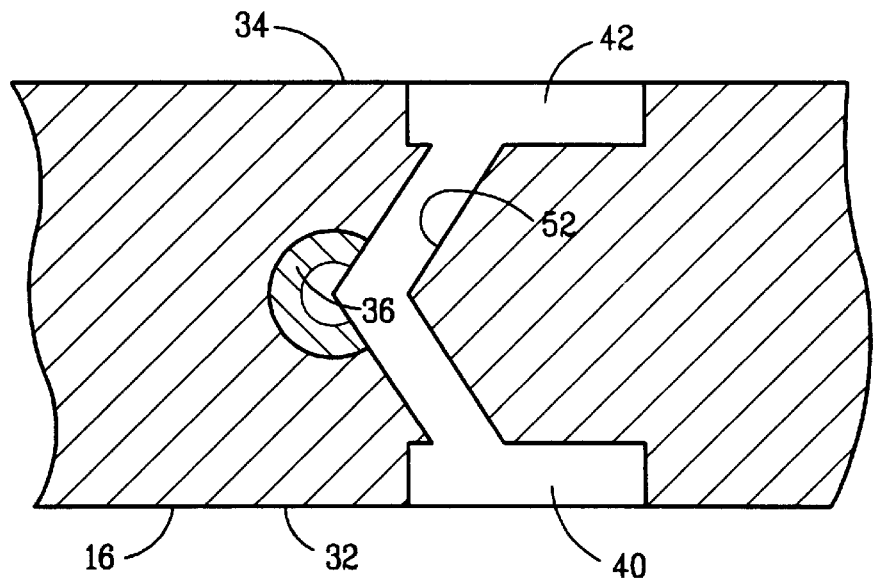
FIG. 10 is a cross-sectional view of a portion of the distributor disk shown in FIG. 9, taken along line X—X.

Referring to FIGS. 5 through 13, each of the plurality of hollow fiber distributor disks 16 is fixedly mounted on the double lumen shaft 14. As shown in FIGS. 7,8,9 and 11, each of the hollow fiber distributor disks 16 comprises an interior surface 28, an exterior surface 30 concentric to the interior surface 28, a first face 32, a second face 34, a first spoke 36 and a second spoke 38 and a plurality of selectively fluid-permeable membrane elements 48. As illustrated in FIGS. 8–11, the first face 32 and the second face 34 each has an arcuate-shaped supply channel 40 and an arcuate-shaped return channel 42. The supply channels 40 and the return channels 42 are spaced apart a distance 44 as illustrated in FIG. 8. As shown in FIGS. 8 and 9, the first spoke 36 defines an oxygen supply path and is connected at its outlet end 39 to the distributor disk 16 and is connected at the inlet end 41 to the oxygen inlet path 29 of the double lumen shaft 14. The second spoke 38 defines a gas return path and is connected at its inlet end 47 to the distributor disk 16 and is connected at the outlet end 46 to the gas outlet path 31 of the double lumen shaft 14. Each of the first and second spokes 36, 38 act as a support for the distributor disk 16. Additional spokes may be added either to increase the number of fluid pathways or provide additional structural support. These spokes may also utilize various cross sectional profiles, such as an airfoil as described below and shown in FIG. 25, to either optimize mixing or provide additional pumping effects.

Figure 11:
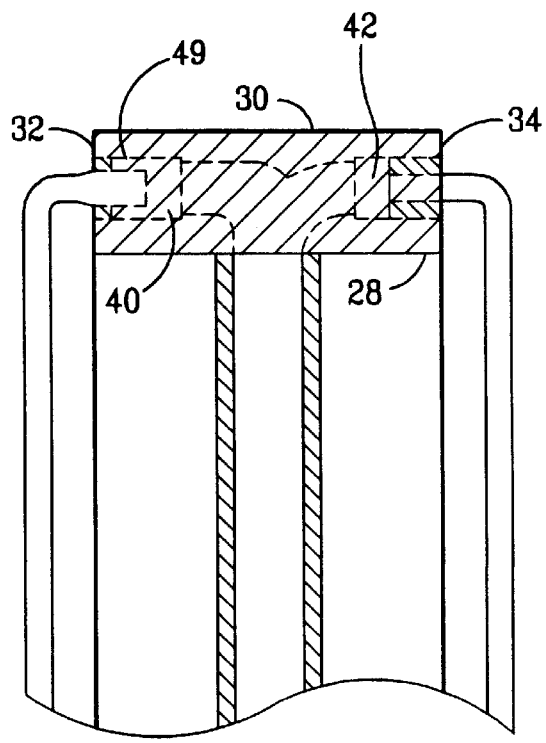
FIG. 11 is a cross-sectional view of a portion of the distributor disk shown in FIG. 9, taken along line XI—XI, which illustrates the fluid connection of the selectively fluid-permeable membrane elements with the channels of the distributor disk.
Figure 12:
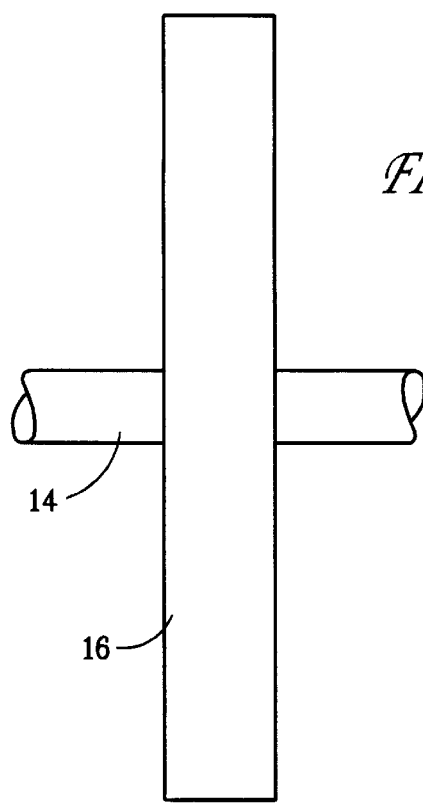
FIG. 12 is a side plan view of the distributor disk shown in FIG. 8.

A plurality of microporous hollow fibers 48 extend across the diameter of the distributor disk 16 and weave around the double lumen shaft 14. Each fiber 48 is connected at one end to the gas supply channel 40 and at its other end to the gas return channel 42. The hollow fibers 48 extend across the first face 32 and the second face 34 of the distributor disk 16. As illustrated in FIG. 11, the plurality of hollow fibers 48 are connected to the supply and return channels 40 and 42, respectively, of the distributor disks 16 by potting material 49, which can be an epoxy resin or polyurethane. In one embodiment, a Y-shaped return tunnel 50 and a Y-shaped supply tunnel 52 shown in greater detail in FIGS. 9, 10 and 11 connect the return and supply channels 42, 40 with the first and second spokes 38 and 36, respectively. The hollow fibers 48 are made from a microporous material, which is permeable to gases and impermeable to liquids. Such microporous hollow fibers are commercially available from a number of suppliers, including Mitsubishi, Akzo Noble, and Hoescht Cellanese. However, if the present invention were used in a kidney dialysis machine, the material of the hollow fibers 48 would necessarily be selectively permeable to liquid. For oxygenation, the preferred material is polypropylene; however, other materials depending upon the application, such as polyethylene, can be used to form the hollow fibers 48.

Figure 13:
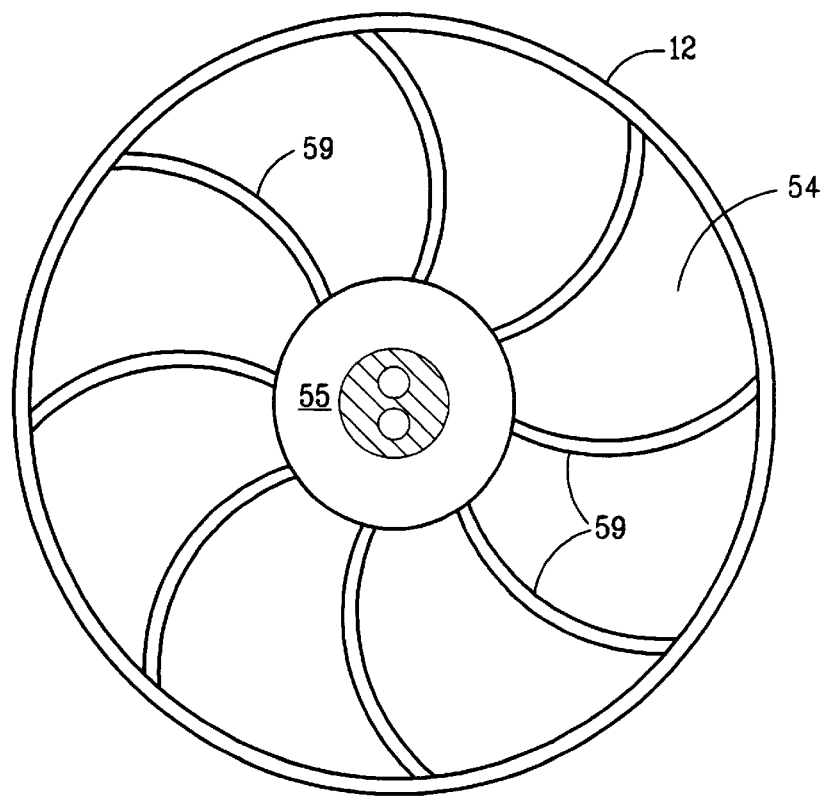
FIG. 13 is a cross-sectional view of the blood membrane oxygenator shown in FIG. 5a taken along line XII–XII.

Sets of baffles 54, shown in greater detail in FIGS. 5 and 13, are preferably interspersed between the distributor disks 16 when more than one distributor disk 16 is used. The baffles 54 are integral members extending from the inner wall of the device housing 12 toward the center of the blood flow path 13, thereby defining a partition 69 within the housing 12 in which a distributor disk 16 will rotate. Each baffle 54 defines a central opening 55 of sufficient area to allow flow from one segment of the housing 12 to the next. Additionally, the surfaces of each baffle 54 preferably includes an elevated rib or flute 59 which serves to provide direction to blood flowing off the surface of the rotating distributing disks 16. The baffle cross section can take many other shapes.

The distributor disks 16 are attached to and rotate about the axis of the double lumen shaft 14. The distributor disks 16 can either rotate in one direction or in a back and forth motion. When rotating in one direction all of the distributor disks rotate in either clockwise or counter-clockwise direction. When the distributor disks 16 are rotating in a back and forth manner each of the distributor disks 16 rotate in one direction for a specified angle and then change directions and rotate in the opposite direction for a specified angle. This back and forth motion agitates the blood surrounding the hollow fibers 48 thus disrupting the blood boundary layer around the hollow fibers. The distributor disks 16 are preferably actuated using a conventional electric motor 60. However, other actuation technologies can be used.

Figure 5A:
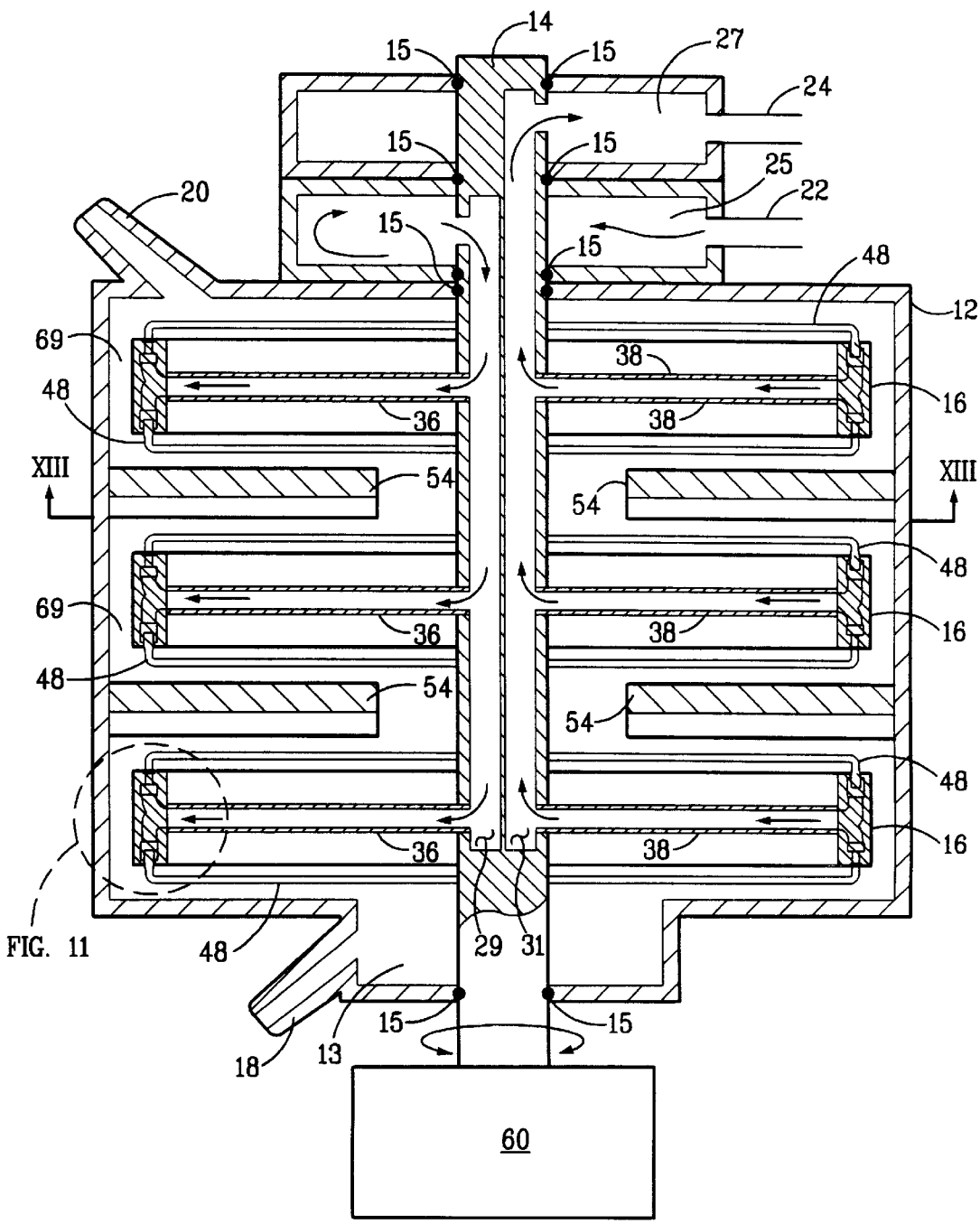
FIG. 5a is a cross-sectional view of the blood membrane oxygenator shown in FIG. 1 taken along line V—V and illustrating the gas flow path and the double lumen shaft of a preferred embodiment.
Figure 5B:
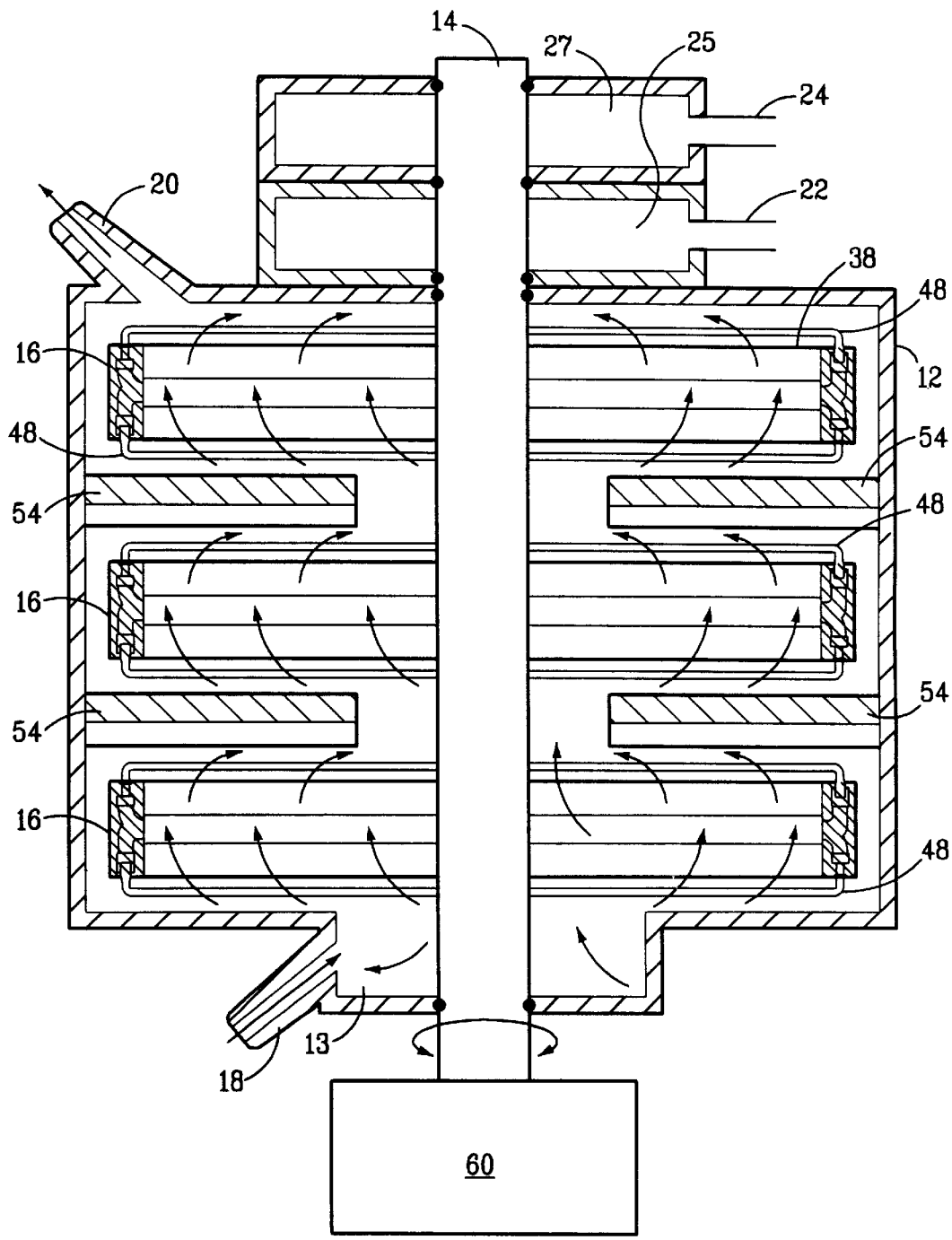
FIG. 5b is the cross-sectional view of the blood membrane oxygenator shown in FIG. 1 taken along line V—V and illustrating the blood flow path.
Figure 6:
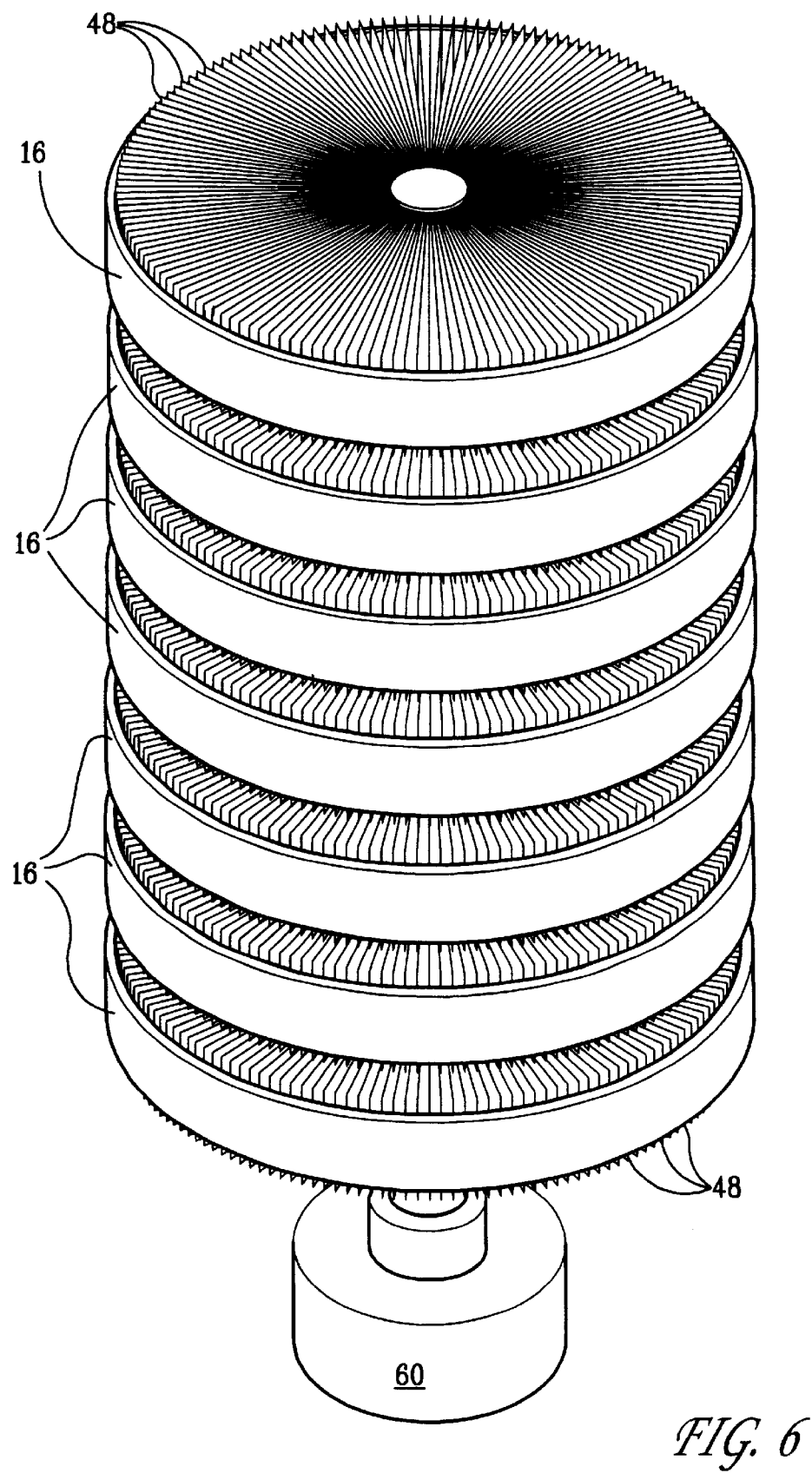
FIG. 6 is a perspective view of a plurality of distributor disks mounted on a double lumen shaft of the blood membrane oxygenator shown in FIG. 1.
Figure 7:
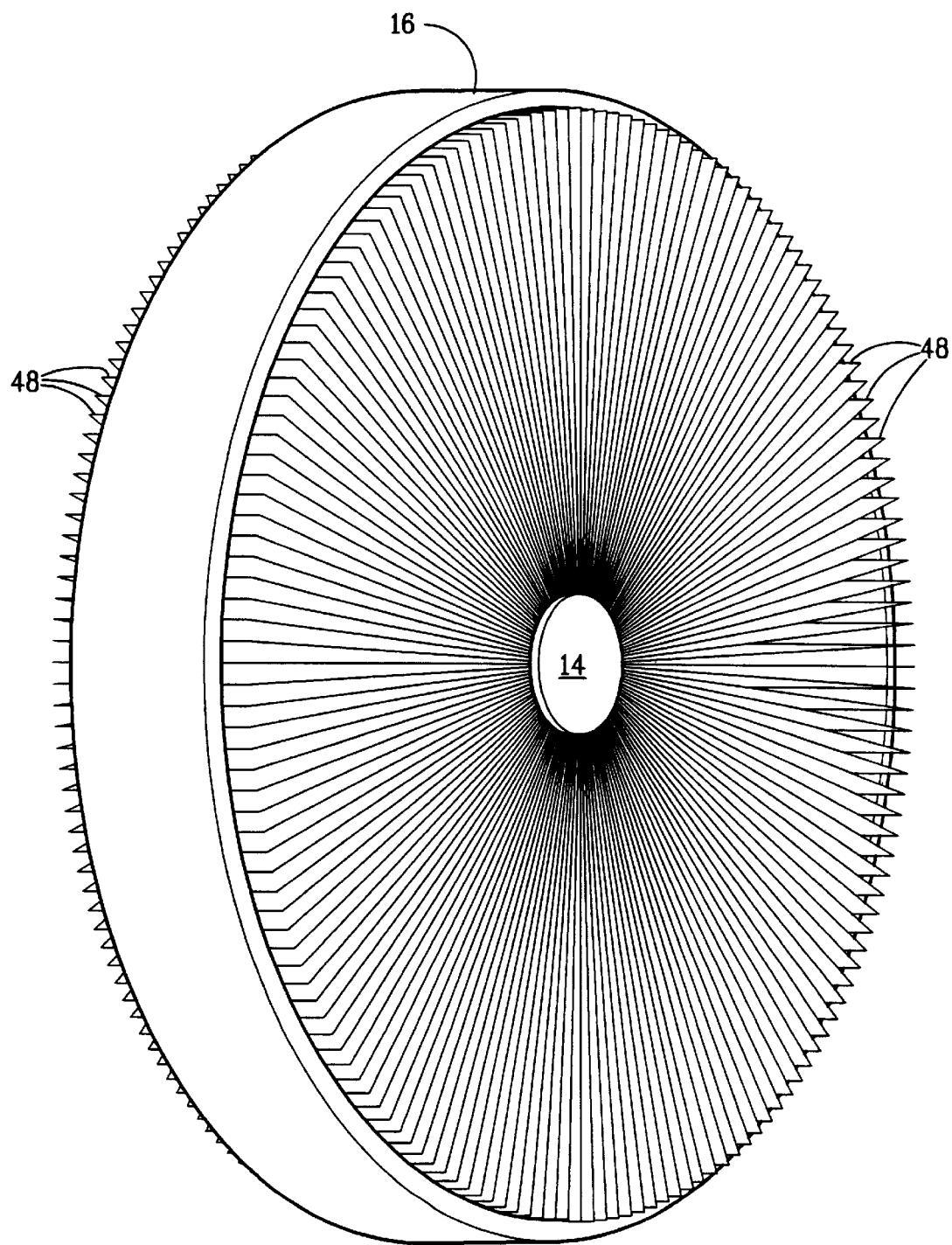
FIG. 7 is a perspective view of one of the distributor disks shown in FIG. 6.

Referring to FIGS. 5A, 5B and 9, the present preferred embodiment provides for the following blood flow paths and oxygen flow paths. Gas containing oxygen enters through the oxygen supply inlet 22, proceeds through the inlet chamber 25, and flows through the oxygen inlet path 29 of the double lumen shaft 14. This "sweet gas" may comprise a mixture of gasses, such as oxygen, nitrogen, and carbon dioxide, as well as other gases within the experience of those of ordinary skill in the art. The oxygen-containing gas then flows into the first spoke 36 which is in fluid communication with the double lumen shaft inlet path 29 at the first spoke inlet end 41. The oxygen then flows through the first spoke 36, through the Y-shaped tunnel 52 and supply channel 40 and enters the lumens of the hollow fibers 48, and flows through the hollow fibers 48 extending across the diameter of the distributor disks 16, where the oxygen exchange takes place. In accordance with the law of diffusion, oxygen, having a high concentration within the lumens of the microporous hollow fibers 48, travels across the walls of the microporous hollow fibers 48 into the venous blood, which has a low oxygen concentration. Simultaneously, carbon dioxide contained in a high concentration within the venous blood travels across the walls of the hollow fibers 48 into the low carbon dioxide concentration lumens of the hollow fibers 48, ultimately flowing to the return gas flow path. The oxygen/carbon dioxide mixture within the hollow fibers 48 enters the return channels 42 of the distributor disks 16 and is transmitted through the Y-shaped return tunnels 50 to the second spoke 38 and then to the gas outlet path 31 of the double lumen shaft 14.

FIG. 9 illustrates gas flow paths when the present invention is utilized as a blood oxygenator. As illustrated by the arrows, oxygen or oxygen-containing gas flows from the oxygen inlet path 29 of the double lumen shaft 29, through the first spoke 36 and into the supply channel 40. The oxygen continues flowing through the lumens of the selectively fluid-permeable fibers 48a. Oxygen diffuses out of the fibers 48a and into the path 13 of the venous blood which flows generally into or out of the page. Simultaneously, carbon dioxide from the venous blood diffuses into the lumens of the fibers 48a, and mixes with oxygen and other gasses that have not diffused from the fibers; this gas mixture flows out of the other end of the fibers 48a into the return channel 42, then to the second spoke 38, and to the gas outlet path 31 of the double lumen shaft 14. This waste gas is then evacuated through the gas outlet 24, which may be connected to a vacuum.

FIG. 9 also illustrates schematically a highly preferred arrangement for the selectively fluid-permeable fibers. In this arrangement, a plurality of fibers 48a are arranged substantially parallel to one another, forming a first layer of fibers. This layer extends substantially across the entire diameter of the distribution disk 16. The spacing has been exaggerated for convenience; in practice, adjacent fibers 48a are close together, even touching one another. Another group of fibers 48b, also arranged substantially parallel to one another, form a second layer of fibers, these fibers 48b being non-parallel with respect to the first layer of fibers 48a, as illustrated.

Referring to FIG. 5B, venous blood enters the blood inlet 18, flows through the flow path defined by the cylindrical portion 13 of the housing 12 where the venous blood contacts the hollow fibers 48 of the rotating distributor disks 16. The venous blood flow path is substantially perpendicular to the hollow fibers 48, as illustrated by the arrows of FIG. 5B, and provides for a degree of mixing and cross-flow of blood, which results in a disruption of the blood boundary layer on the hollow fibers 48. Further, the rotation of the hollow fibers 48 on each of the distributor disks 16 and the presence of the baffles 54 between the rotating distributor disks 16 provides for a greater degree of mixing of blood, resulting in enhanced oxygenation. The venous blood directly contacts and surrounds the walls of the hollow fibers 48 providing three-dimensional oxygenation. The oxygen-enriched blood then exits through the arterial blood outlet

20. By rotating the distributor disks 16, which carry the hollow fibers 48 through the venous blood, three dimensional mixing and efficient oxygenation are realized. The rotation of the distributor disks 16 also results in a significant degree of pumping of the blood through the housing 12.

Figure 14:
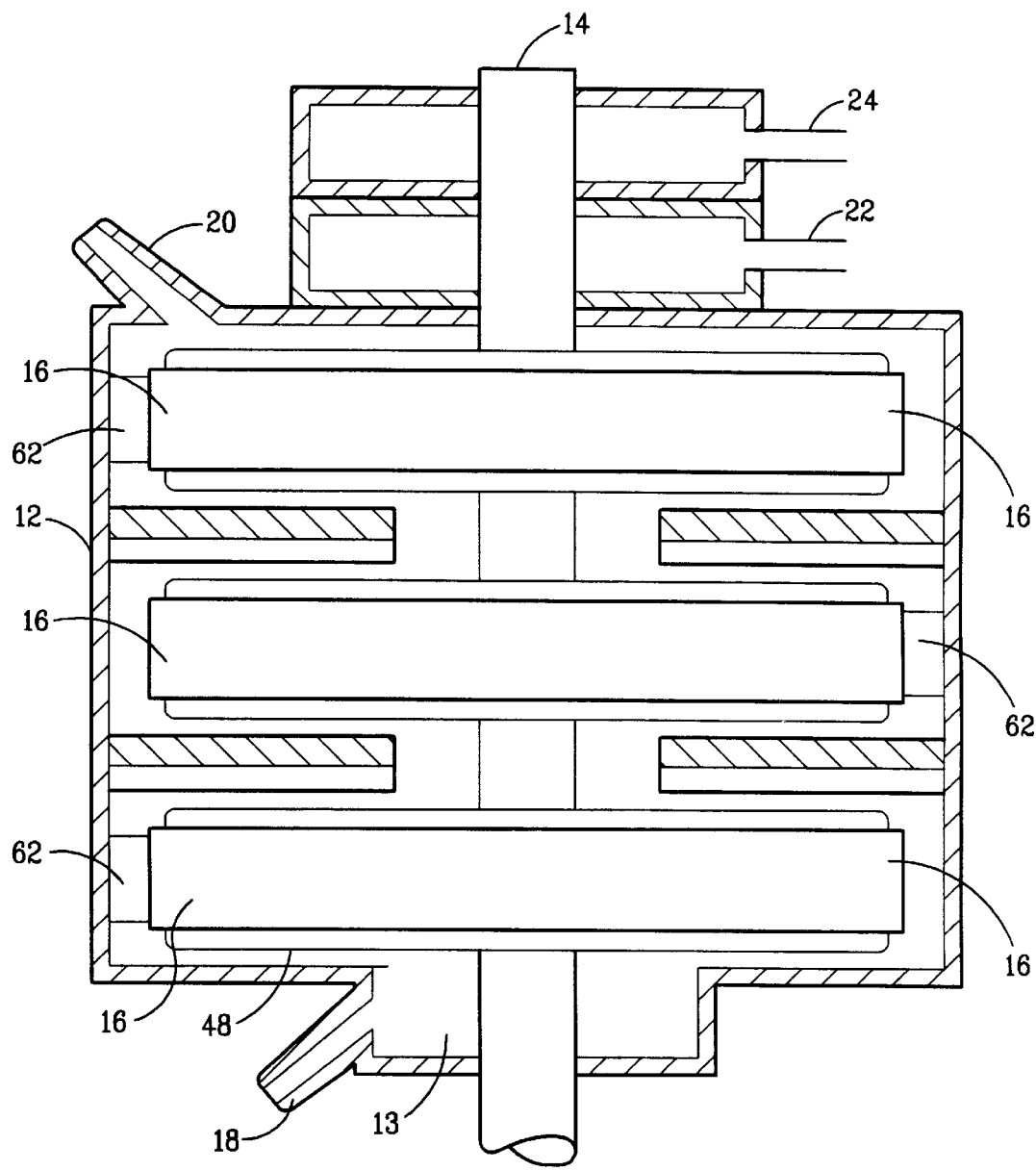
FIG. 14 is an alternative embodiment of the invention, being a cross-sectional view of a blood membrane oxygenator similar to the blood membrane oxygenator shown in FIG. 5a, which employs a series of drive rollers to impart rotational movement to the distributor disks.

Referring to FIG. 14, alternating counter-rotation of the distributor disks 16 can be achieved by a series of drive rollers 62, rotating in opposite directions, which firmly contact the outer edge of the distributor disks 16, thereby imparting rotational movement to the distributor disk 16. When rotating in the alternating counter-rotation manner some of the distributor disks 16 rotate clockwise while the other distributor disks 16 simultaneously rotate counter-clockwise. This alternating counter-rotation provides for disruption of the boundary layer of blood contacting the hollow fibers 48 resulting in increased oxygenation. Alternatively, the disks 16 could be mounted on coaxial shafts, which are turned in opposite directions to impart counter-rotation of the alternating distributor disks 16.

Figure 15:
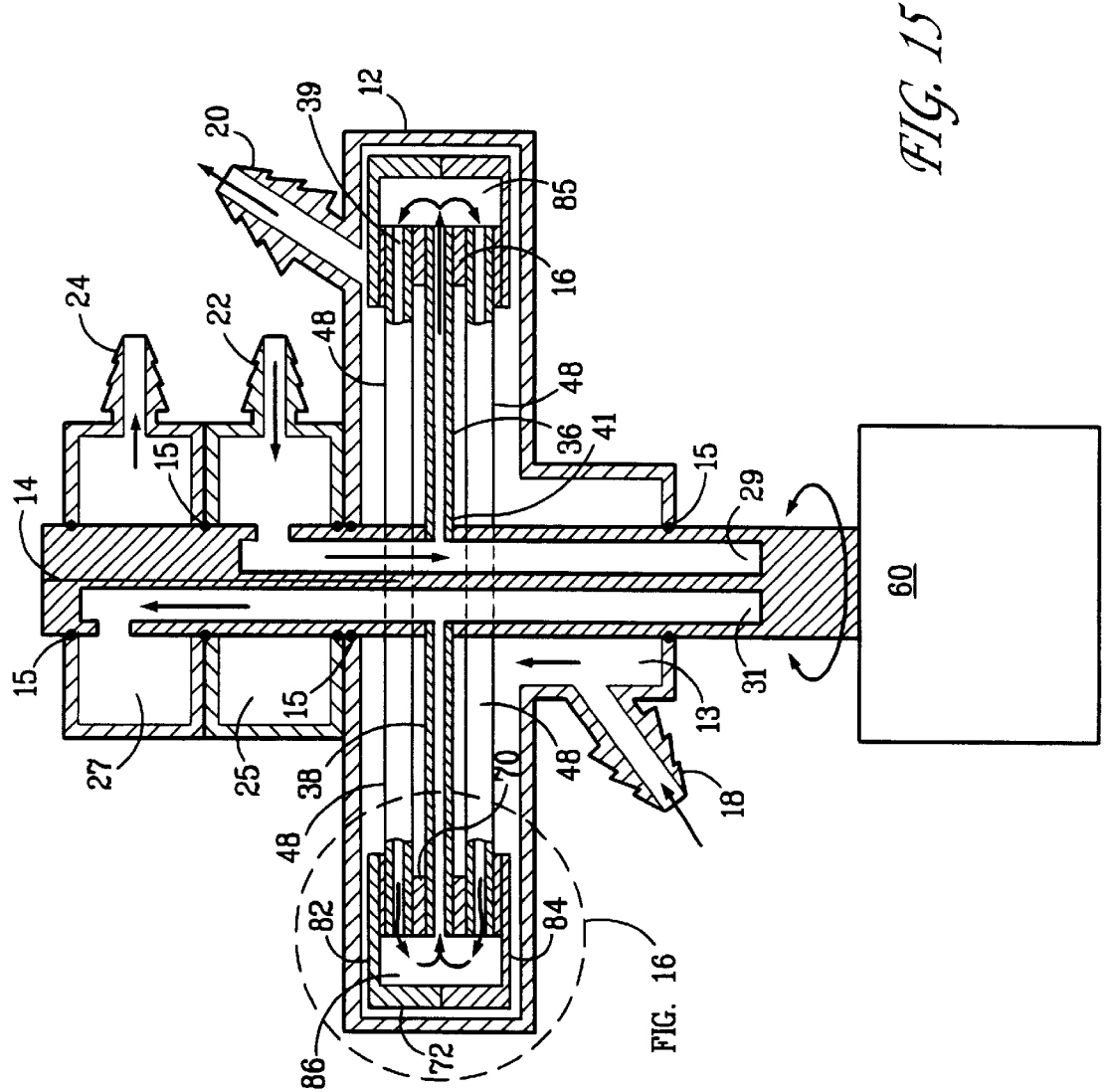
FIG. 15 is cross-sectional view of a preferred blood-pump oxygenator of the present invention.
Figure 16:
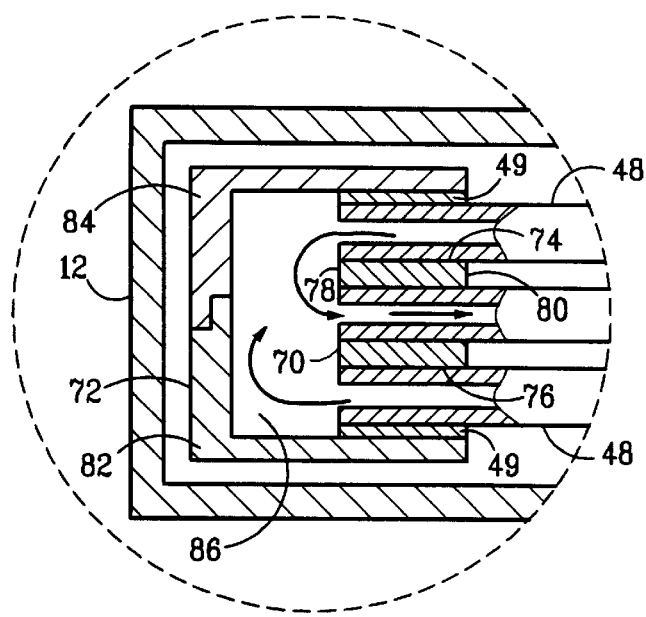
FIG. 16 is an enlarged view of a distributor element shown in FIG. 15 illustrating the fluid connection of the selectively fluid-permeable membrane elements with the channels of the distributor disk.
Figure 17:
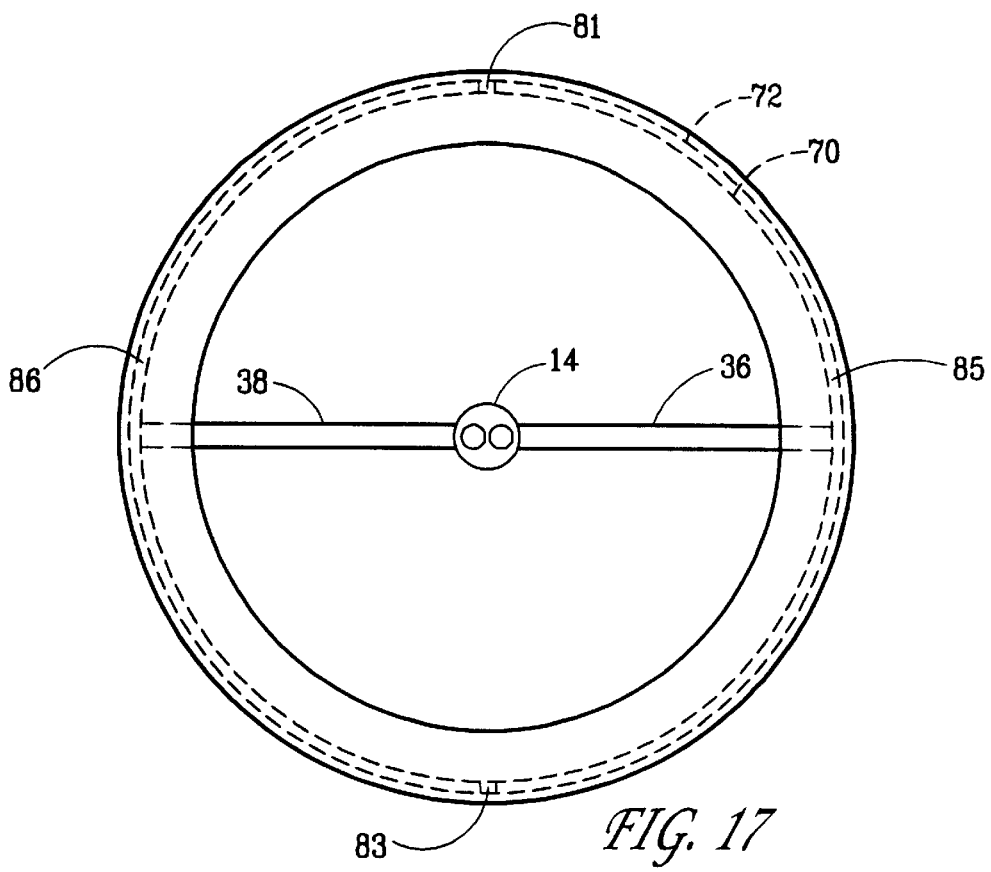
FIG. 17 is a side plan view of the retaining ring of the distributor element of the blood-pump oxygenator shown in FIG. 15.

FIGS. 15 through 17 illustrate another highly preferred embodiment of a blood pump-oxygenator of the present invention. Elements of the different embodiments of the present invention, which are similar, are referred to using the same reference numerals. The blood-pump oxygenator 10 substantially comprises a housing 12, a rotor hub in the form of a double lumen shaft 14, a single distributor disk 16 and a motor 60 connected to the double lumen shaft 14. The housing 12 defines a blood flow path 13 and has a venous blood inlet 18, an arterial blood outlet 20, a gas inlet chamber 25 with a gas inlet 22 and a gas outlet chamber 27 with a gas outlet 24. Seals 15 isolate the various blood and gas flow chambers as previously described. A vacuum may be drawn on the gas outlet 24 to further assist in achieving the desired gas flow. The housing 12 can take a variety of forms; however, it is preferred that the housing 12 be substantially cylindrical and be as small as possible in order that the blood priming volume be minimized.

The double lumen shaft 14 is rotatably connected to the cylindrical housing 12 and extends along the longitudinal axis of the housing 12. The shaft 14 is connected to a motor 60 at one end thereof The motor is preferably a conventional brushless DC motor; however, any type of device that will agitate the shaft 14 can be used. The shaft 14 defines a gas inlet path 29 and a gas outlet path 31. The shaft 14 is connected to the distributor disk 16 by a first spoke 36 and a second spoke 38. The first spoke 36 is in fluid communication with the gas inlet path 29 and the second spoke 38 is in fluid communication with the gas outlet path 31.

The distributor disk 16 has an inner ring 70, a two-piece outer ring 72 and a plurality of microporous selectively fluid-permeable membrane elements 48. Referring to FIG. 16, the inner ring 70 has a first face 74, a second face 76, an exterior surface 78 and an interior surface 80. The outer ring 72 has a first ring member 82 with a substantially L-shaped cross-section and a second ring member 84 also with a substantially L-shaped cross-section. The two ring members 82 and 84 are fixedly attached to one another preferably with an adhesive such that the short legs of each of the L-shaped cross sections are joined. As illustrated in FIG. 15, the two piece outer ring 72 is positioned around the inner ring 70 such that a gas supply plenum 85 and a gas return plenum 86 are formed between the inner ring 70 and the outer ring 72 and extends around the circumference of the inner ring 70. Two dividers 81 and 83 (illustrated in FIG. 17) extending between the inner ring 70 and the outer ring 72 separate the gas supply plenum 85 from the gas return plenum 86. The plurality of microporous selectively fluid-permeable membrane elements 48 extend across the diameter of the distributor disk 16 and pass adjacent to the double lumen shaft 14 such that the plurality of microporous selectively fluid-permeable membrane elements 48 are inserted between the first face 74 of the inner ring 70 and the outer ring 72 and the second face 76 of the inner ring 70 and the outer ring 72 and are in fluid communication with the gas plenums 85 and 86. The plurality of selectively fluid-permeable membrane elements 48 are sealed to the distributor disk using a potting material 49, which can be an epoxy resin.

The selectively fluid-permeable membrane elements 48 are made from a microporous material, which is selectively permeable to various fluids depending on the use of the device. Preferably, the microporous material is a layer of membrane elements. If the device is used for oxygenation, the preferred material is polypropylene; however, other materials such as polyethylene can be used to form the selectively fluid-permeable membrane elements 48. If the present invention is used in a kidney dialysis machine the material of the selectively fluid-permeable membrane elements 48 would be permeable to various substances such as salts, ammonia and creatine.

The motor 60 imparts rotation to the shaft 14, which rotates the distributor disk 16 about the longitudinal axis of the double lumen shaft 14. The distributor disk 16 can either rotate in one direction or in a back and forth motion. When rotating in one direction the distributor disk rotates in either clockwise or counter-clockwise direction. When the distributor disk 16 is rotating in a back and forth manner the distributor disk 16 rotates in one direction for a specified angle and then change direction and rotates in the opposite direction for a specified angle. These angles need not be the same. If the angles differ, pumping is achieved via an absolute disk precession. This back and forth motion agitates the blood surrounding the selectively fluid-permeable membrane elements 48, thus disrupting the blood boundary layer. It should be understood that additional distributor disks 16 can be added and the distributor disks 16 can also be counter-rotated as described when referring to FIG. 14.

Referring to FIG. 15, the present preferred embodiment provides for the following blood flow paths and oxygen flow paths. Oxygen (or an oxygen-containing gas mixture, e.g. air) enters through the oxygen supply inlet 22, proceeds through the inlet chamber 25, and flows through the oxygen inlet path 29 of the double lumen shaft 14. The oxygen then flows into the inlet end 41 of the first spoke 36, which is in fluid communication with the double lumen shaft inlet path 29. The oxygen then flows through the first spoke 36 to the first spoke outlet end 39 and into the gas supply plenum 85. From the gas supply plenum 85, the gas enters the selectively fluid-permeable membrane elements 48 extending across the diameter of the distributor disks 16 where the oxygen exchange takes place. In accordance with the law of diffusion, oxygen travels across the walls of the microporous selectively fluid-permeable membrane elements 48 and into the venous blood, while simultaneously, carbon dioxide contained within the venous blood travels across the walls of the selectively fluid-permeable membrane elements 48. The oxygen/carbon dioxide mixture exits the selectively permeable membrane elements 48 and enters the gas return plenum 86, which is in fluid communication with the second spoke 38 and through which the oxygen/carbon dioxide mixture travels to the gas outlet path 31 of the double lumen shaft 14, exiting through the gas outlet 24.

While the oxygen is following the above-described flow path through the blood pump-oxygenator of the present invention, venous blood is collected from the patient via cannulae surgically placed within the venous system. Such venous blood is conducted to the pump/oxygenator venous blood inlet through flexible plastic tubing commonly used for such purposes. As will now be readily apparent to one of ordinary skill in the art, anticoagulants such as heparin can be advantageously employed to minimize formation of blood clots in the oxygenation system of the invention. In some cases it may be necessary to interpose a blood reservoir between the venous collection cannulae and the venous blood inlet of the pump/oxygenator in order to compensate for physiologic and/or mechanical alteration in the balance between blood inflow from the patient and blood return to the patient. Venous blood so acquired is introduced into the pump/oxygenator by passive inflow into the blood inlet 18 and is pumped through the cylindrical portion 13 of the housing 12 where the venous blood contacts the selectively fluid-permeable membrane elements 48 of the rotating distributor disks 16. The bulk flow path of the venous blood is substantially perpendicular to the selectively fluid-permeable membrane elements 48 and provides for a degree of mixing and cross-flow of blood, which results in a disruption of the blood boundary layer on the membrane elements 48. Further, pure rotation of the selectively fluid-permeable membrane elements 48 on each of the distributor disks 16 provides for a greater degree of mixing of blood resulting in enhanced oxygenation/decarbonation and pumping. The venous blood directly contacts and surrounds the walls of the selectively fluid-permeable membrane elements 48 providing three-dimensional oxygenation. The oxygen-enriched blood then exits the pump/oxygenator through the arterial blood outlet 20 where it is delivered to the patient's arterial circulation via a flexible plastic conduit and an arterial return cannula surgically inserted into an appropriate vessel. Other devices, such as arterial blood filters or bubble traps may be electively inserted into this arterial return circuit in some clinical situations. The rotating distributor disks 16 pump blood through the housing 12 such that when the blood exits the housing 12 at the arterial exit 20, the blood has more energy than when the blood entered the housing 12 at the blood inlet 18.

Figure 18:
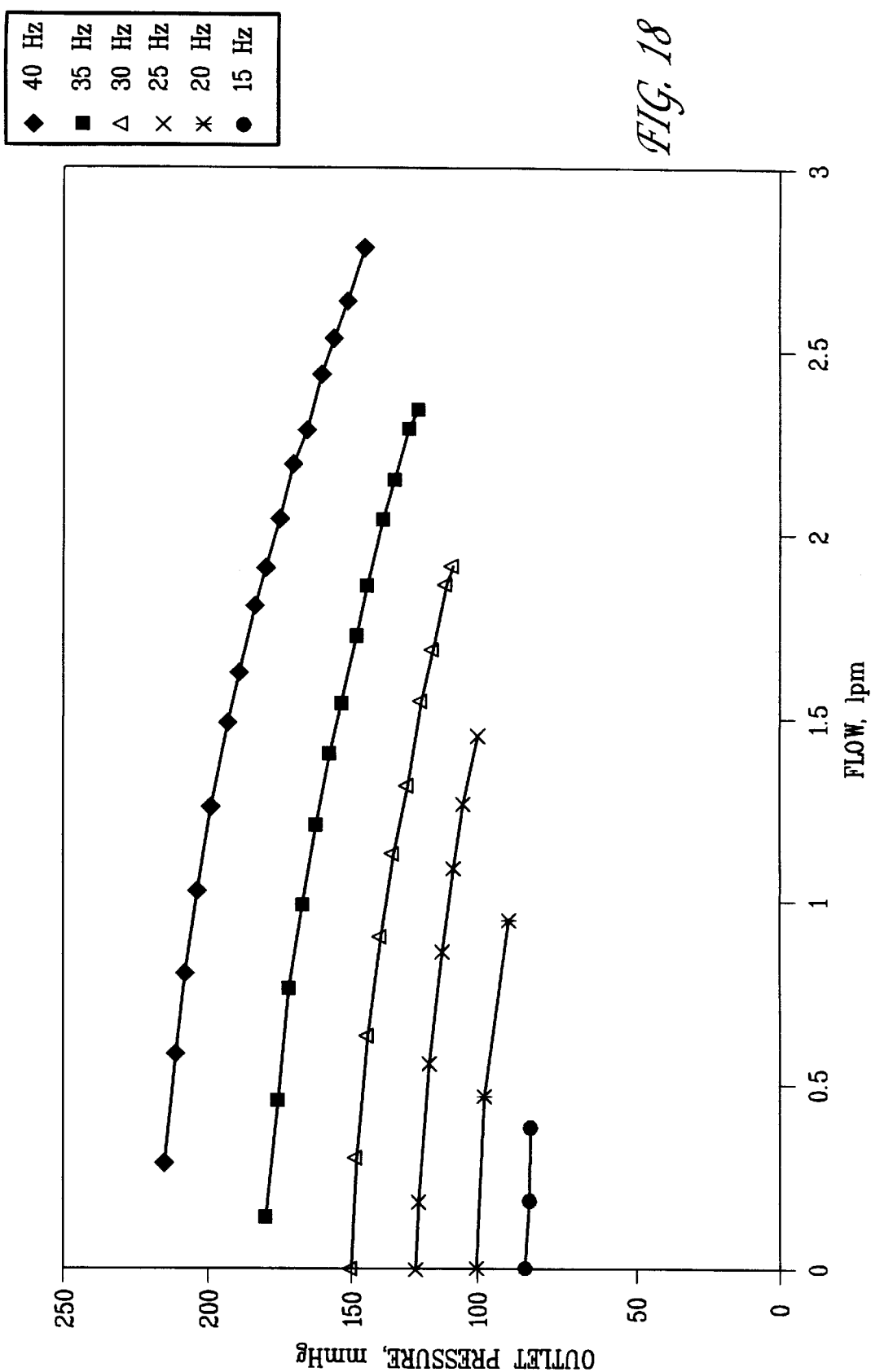
FIG. 18 is a graph, which illustrates the pumping ability of the blood pumpoxygenator shown in FIG. 15 and charts flow in liters per minute versus output pressure in millimeters of mercury.

The pumping capability of the present invention pump-oxygenator is illustrated in FIG. 18. A blood pump-oxygenator of the present invention having one distributor disk 16, substantially as that shown in FIGS. 15 through 17, was rotated continuously unidirectionally and deionized water entered the housing 12 through inlet 18. The results of this test are shown in FIG. 18, which is a graph that charts the pressure rise in the mass transfer and pump apparatus of the present invention versus the flow rate. Each curve represents a speed of operation. As can be seen, the pressure generated due to device rotations is significant.

Figure 19:
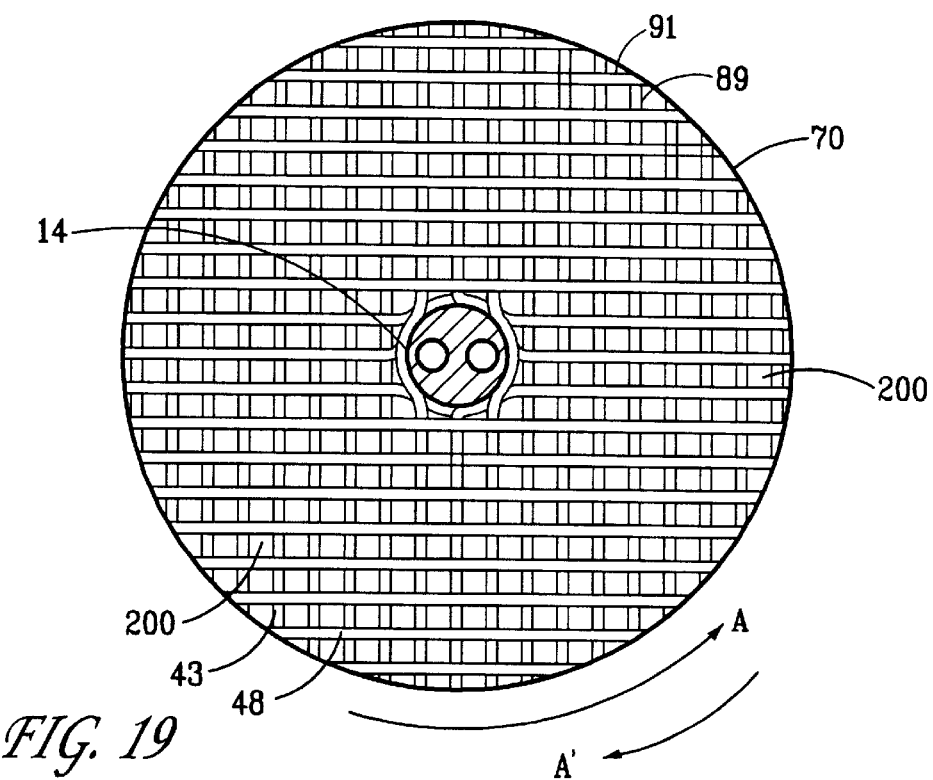
FIG. 19 is a side plan view of an alternate embodiment of the distributor element of the blood pump-oxygenator of the present invention having two layers of selectively fluid-permeable membrane elements.

FIG. 19 illustrates an alternate highly preferred embodiment of the distributor disk 16 of the blood pump-oxygenator of the present invention which has two layers 89 and 91 of selectively fluid-permeable membrane elements 48 placed across the diameter of the inner ring 70 such that the selectively fluid-permeable membrane elements 48 of one layer 89 are perpendicular to the selectively fluid-permeable membrane elements 48 of the other layer 91. By increasing the layers of selectively fluid-permeable membrane elements 48, oxygenation will increase. As illustrated, the selectively fluid-permeable membrane elements form a mesh that includes openings or pores 200 through which blood or other liquid flows. These pores 200 allow the disk 16 to operate as a pump when rotated and/or agitated back and forth with precession, as illustrated by the arrows A, A'. These arrows A, A' demonstrate a scenario in which the disk 16 rotates in a wide sweep A, then counter rotates in a narrower sweep A'. This results in liquid flow normal to the page.

Figure 20:
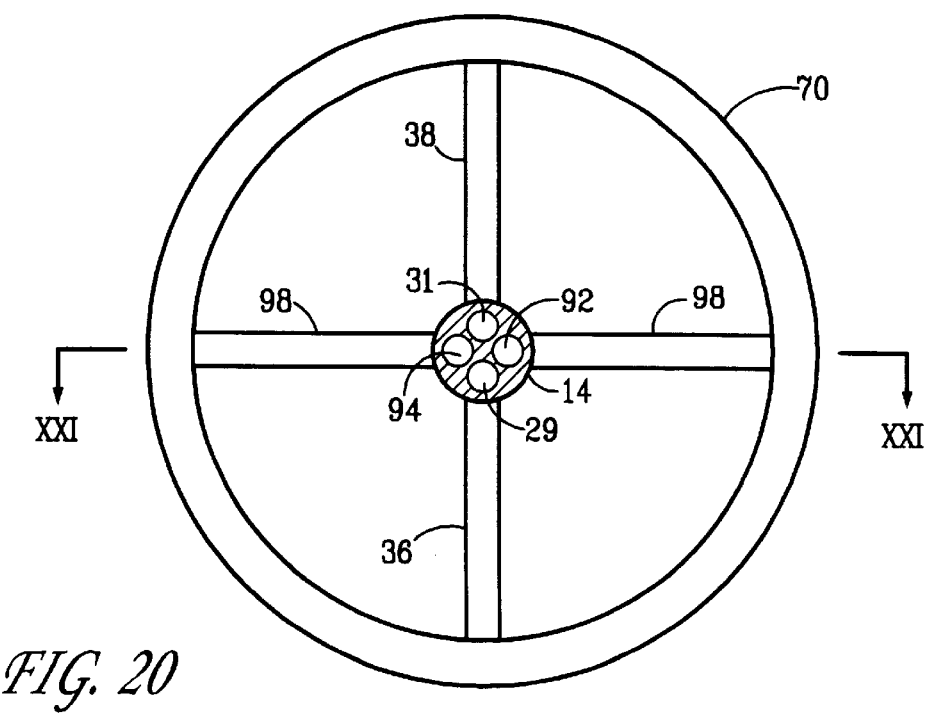
FIG. 20 is a partial side sectional view of an alternative embodiment of the distributor element of the present invention blood pump-oxygenator, which incorporates a heat exchanger and eliminates the selectively fluid-permeable membrane elements for clarity.
Figure 21:
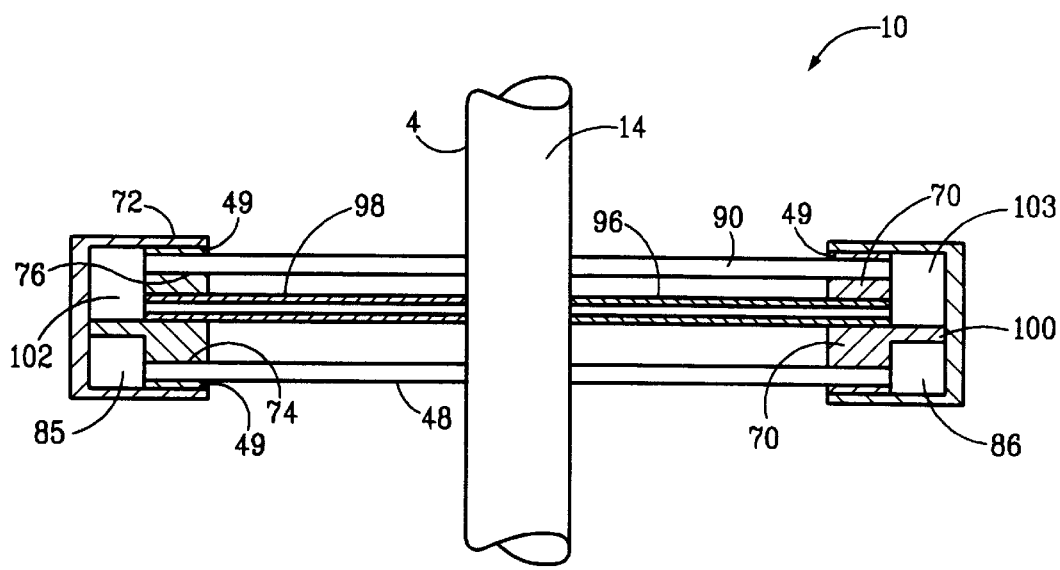
FIG. 21 is a cross-sectional view of the distributor element shown in FIG. 20 taken along line XXI—XXI.

FIGS. 20 and 21 illustrate an alternative embodiment of the present invention that incorporates a heat exchanger. Except where distinguished, the configuration of the blood pump-oxygenator 10 illustrated in FIGS. 20 and 21 is substantially the same configuration as that disclosed in FIGS. 15 through 17. The integrated heat exchanger takes the form of fluid-impermeable membrane elements 90, which carry a fluid and extend across the diameter of the inner ring 70. In addition to the gas inlet path 29 and the gas outlet path 31 of the shaft 14, the shaft 14 has a heat exchanger fluid inlet path 92 and a heat exchanger fluid outlet path 94 parallel to the gas inlet and outlet paths 29 and 31. A fluid supply spoke 96 and a fluid return spoke 98 extending between the inner ring 70 and the shaft 14 are in fluid communication with the fluid inlet path 92 and fluid outlet path 94, respectively. The inner ring 70 further has a divider 100 which divides the space defined by the two piece outer ring 72 and the inner ring 70 into gas supply and return plenums 85 and 86 and heat exchanger fluid supply and return plenums 102 and 103. The fluid-impermeable membrane elements 90 extend across the second face 76 of the inner ring 70 and the selectively fluid-permeable membrane elements 48 extend across the first face 74 of the inner ring 70. Both selectively fluid-permeable membrane elements 48 and fluid-impermeable membrane elements 90 are attached to the inner ring 70 and the outer ring 72 with potting material 49 which can be either resin or polyurethane.

In operation, the heat exchanger fluid, which is preferably water, is introduced into the fluid inlet path 92, through the fluid supply spoke 96, into the fluid supply plenum 102 and then through the fluid-impermeable membrane elements 90. The blood that is being pumped through the housing 12 contacts the fluid-impermeable membrane elements 90 and is heated or cooled by convection via an imposed thermal gradient. Upon exiting the fluid-impermeable membrane elements 90, the water or other heat exchanger fluid enters the fluid return spoke 96 through which it is transported to the fluid outlet path 94. This type of heat exchanger can be used to cool as well as heat a fluid depending on the application.

Figure 22:
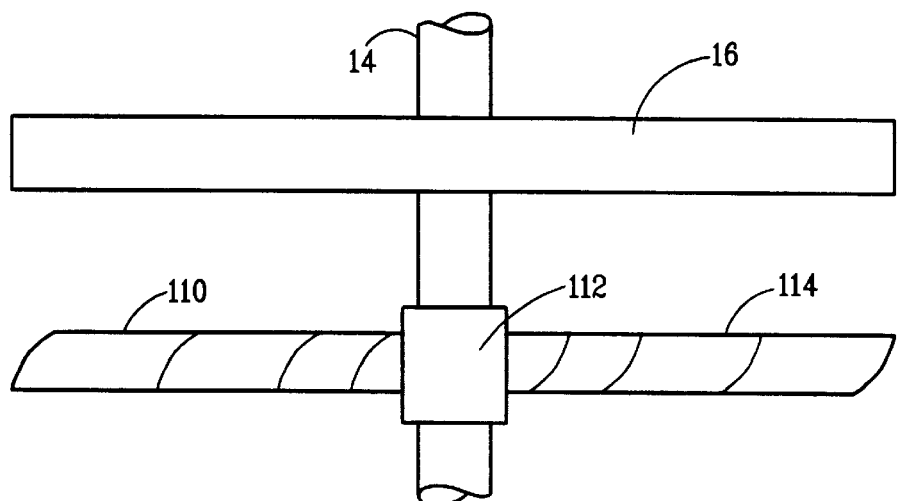
FIG. 22 is a side plan view of an embodiment of the blood pump-oxygenator of the present invention having an impeller member.
Figure 23:
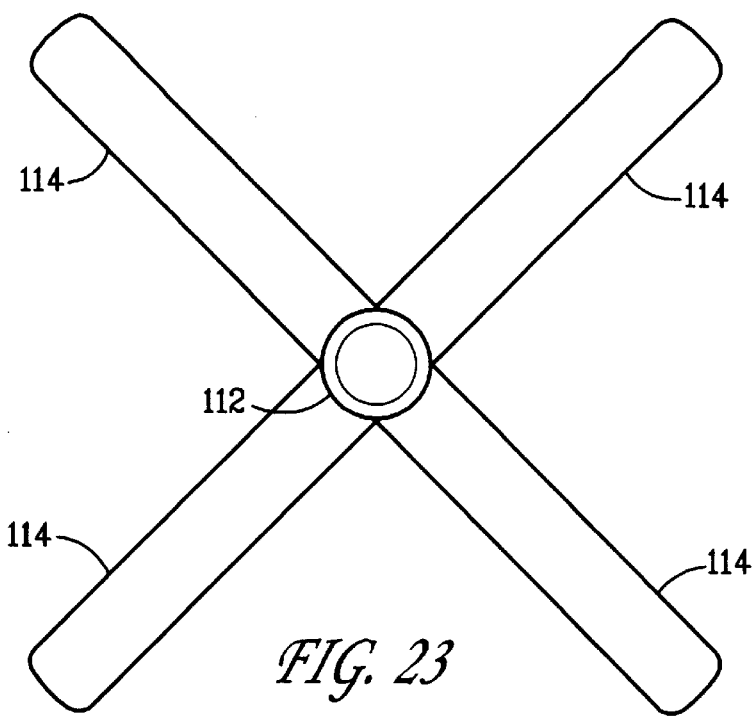
FIG. 23 is a top view of the impeller shown in FIG. 22.
Figure 24:
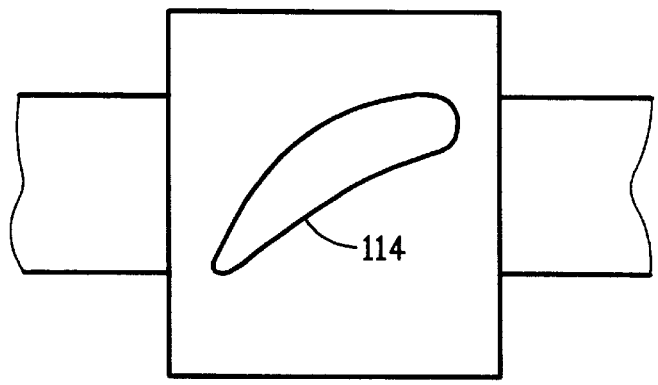
FIG. 24 is a side view of the impeller shown in FIG. 22 illustrating the cross-section of one blade of the impeller.

FIGS. 22 through 24 illustrate an alternate embodiment of the blood pump-oxygenator of the present invention, which incorporates an impeller 110. The impeller has a tubular hub 112 and four blade members 114 radiating from the hub 112. As can be seen in FIG. 24, the blade members 114 have an airfoil cross-section. The hub 1 12 is fixedly attached to the shaft 14 and rotates with the shaft 14 resulting in increased pumping of venous blood through the housing 12. It should be noted that the impeller blade members 114 may be present in more or less than four blade members, and that the blade members could assume shapes that are fluidynamically streamlined, but different from that depicted.

Figure 25:
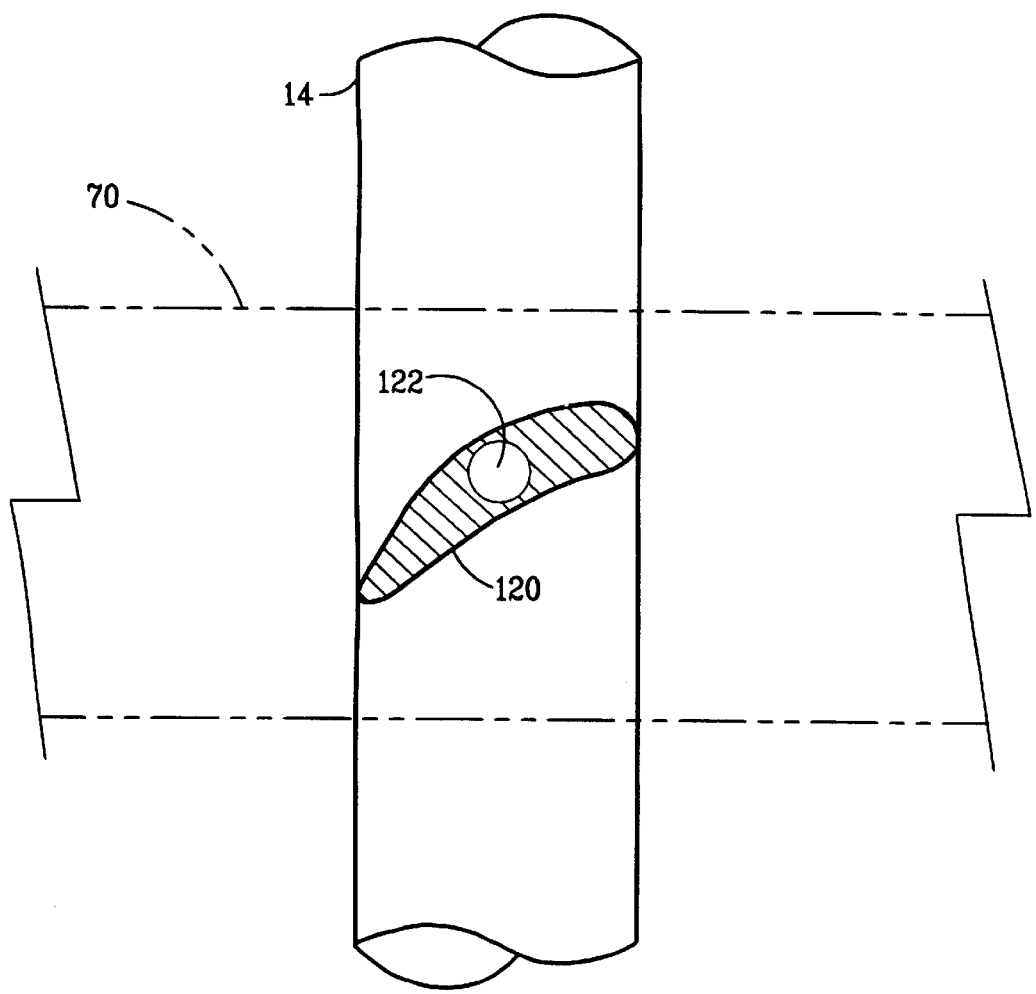
FIG. 25 is a side view of an embodiment of the distributor element of the present invention having an airfoil spoke and illustrating the retaining ring with hidden lines.

FIG. 25 illustrates an alternate embodiment of the distributor disk 16 of the present invention having a spoke 120 that is configured to be fluidynamically streamlined and thereby increase the pumping efficiency of the integrated pump-oxygenator of the present invention. The spoke 120 has a cross-section sized and proportioned such that the spoke rotating through blood will not cause turbulent flow but will increase the pumping capabilities of the present invention. The spoke 120 defines fluid path 122. This type of spoke can be incorporated into the blood pump-oxygenator shown in FIGS. 15 through 17 by substituting spoke 120 for spokes 36 and 38. Although the spoke 120 is shown as an airfoil, it need not be; for example, a preferred embodiment might alter the shape of the spoke 120 to be streamlined, not to pump, but minimize turbulence caused by the spoke 120.

EXAMPLES

1) Blood Oxygenation

Figure 26:
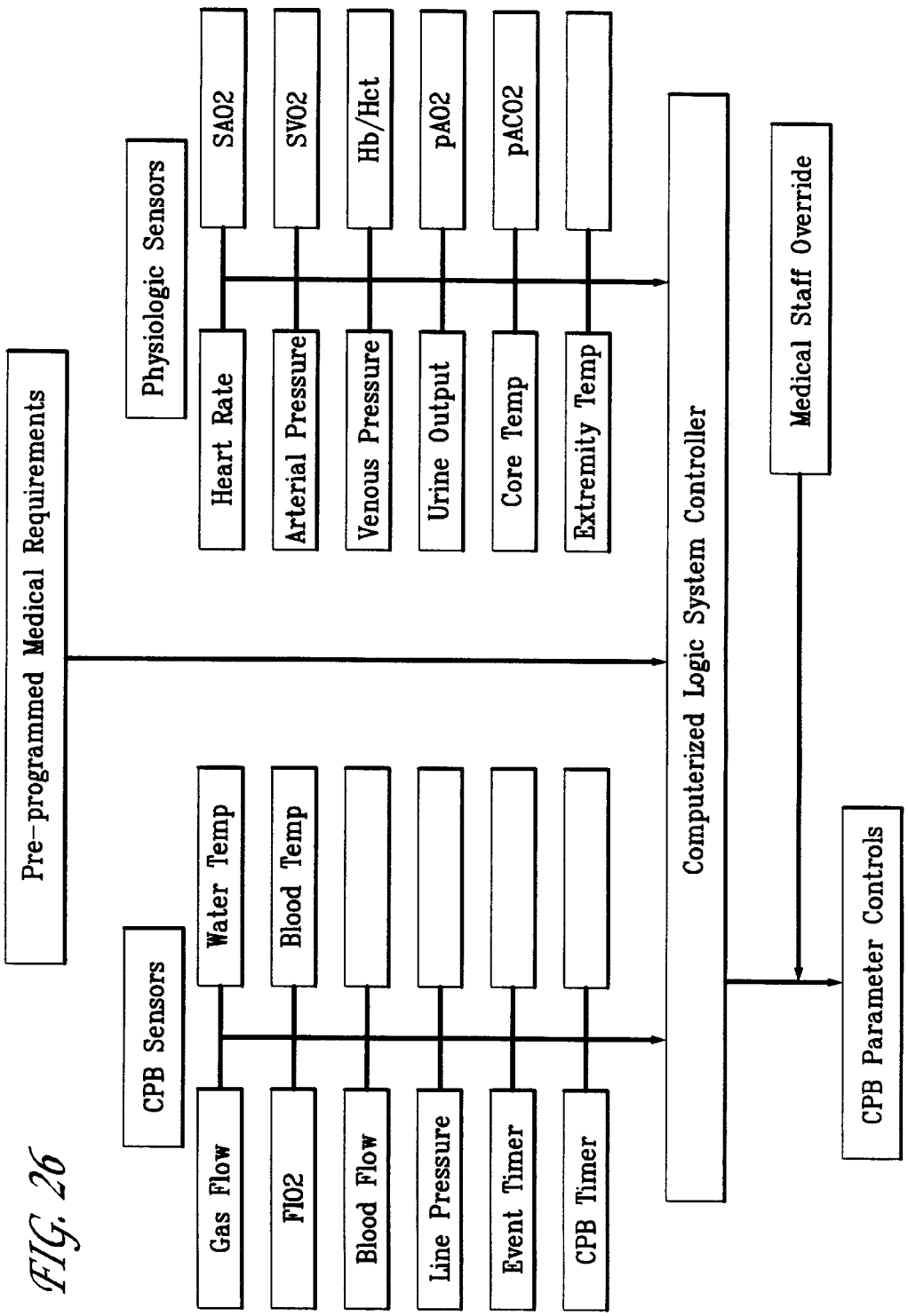
FIG. 26 is a schematic illustration of a block diagram for smart controller useful in practicing a preferred embodiment of the invention.

The mass and heat transfer and pump apparatus described above can be adapted for use in the oxygenation of blood, for example during open-heart surgery. As noted above, for this application the preferred material of the hollow fibers 48 would be a compound such as polypropylene which is permeable to oxygen and carbon dioxide but impermeable to blood. With such materials the apparatus can provide oxygen to a patient's blood extracorporeally and remove waste gases before the blood is returned to the patient. One skilled in the blood oxygenation field will recognize that the apparatus of the present invention can be used in a variety of cardiac surgical procedures and used in connection with a variety of other life support systems such as those described in U.S. Pat. No. 5,752,526 issued to Cosgrove et al. and U.S. Pat. No. 5,725,544 to Rygaard et al., the disclosures of which are hereby incorporated by reference in their entirety. FIG. 26 illustrates a block diagram of the parameters that could be incorporated into a control system for operation of the described device as a blood oxygenator.

2) Cardiopulmonary Bypass Support

The heart-lung machine used for cardiopulmonary bypass support of the cardiac surgical patient is, in reality, a system of interconnected disposable devices/circuits used to support the patient's circulation and respiration. The system normally contains the following circuits:

1. The primary (and physiologically most important) circuit is the veno-arterial-artificial oxygenator loop through which the patient's venous blood is propelled by a mechanical pump, oxygenated and decarbonated by the artificial oxygenator and returned to the patient's arterial circulation to support the patient's physiologic needs. It is this circuit (and function) that keeps the patient alive during the time the surgeon works on the usually non-beating heart. Operationally, in this circuit venous blood is collected from the patient via cannulae surgically placed within the venous system. Such venous blood is conducted to the oxygenator venous blood inlet through flexible plastic tubing commonly used for such purposes. Usually it is necessary to interpose a blood reservoir between the venous collection cannulae and the venous blood inlet of the mechanical pump in order to compensate for physiologic and/or mechanical alteration in the balance between blood inflow from the patient and pump assisted blood inflow into the artificial oxygenator. In most current systems venous blood so acquired is introduced into the oxygenator by active propulsion generated by discrete mechanical pump(s). Due to fluid flow resistance encountered within the artificial oxygenator a significant blood pressure drop is normally expected across the oxygenator. Accordingly, the inflow pump must be regulated to generate adequate inlet pressure (at the oxygenator inlet) in order to maintain sufficient outlet pressure. This is required to properly propel the arteriolized blood through the remaining flexible conduit of the circuit where it is reintroduced into the patient's arterial vascular system through a surgically attached cannula. Such "arterial reintroduction" must be flowrate controlled to meet the physiologic requirements of the patient. Inadequate and/or excessive flowrate may produce significant clinical compromising of the patient.

2. A "coronary" or pericardial suction circuit is included which provides for aspiration and salvage of blood spilled into the surgical wound (pericardial and sometimes pleural spaces). This blood is aspirated as needed from the surgical site utilizing a suction wand, small (¼" id) PVC tubing and reverse rotation of a roller pump. This extravascular, salvaged blood is passed through a cardiotomy reservoir where it is filtered and then reintroduced into the general circulation of the patient via a conduit connection within the A-V loop discussed in circuit #1 above.

3. A "ventricular vent" circuit (which is similar in construction to the circuit described above for pericardial suction) is utilized to keep the heart decompressed during the time the patient is on total bypass. Even during "total bypass" some blood may circumvent the venous return cannulae, intended to divert venous blood into the extracorporeal circuit, and thereby gain entrance into the chambers of the heart. Additionally, collateral circulation from the lungs and coronary flow into the coronary sinus adds to potential fluid collection within the chambers of the heart. If such fluid/blood collection is not evacuated on a timely basis distention of the ventricular chambers may result in significant impairment of cardiac function. Consequently, a ventricular vent circuit is utilized to keep a semi-continuous aspiration of fluid from the left ventricle as a protective measure. Any fluid aspirated from this circuit is introduced into the cardiotomy reservoir (described in circuit #2 above) where it is commingled with pericardial salvaged blood before reintroduction into the general circulation as previously described.

4. A "cardioplegia circuit" is typically included with the heart lung machine system, especially if the cardioplegic solution is to be admixed with blood prior to administration into the coronary vascular system of the heart. Such administration is utilized to protect the ischemic myocardium during the time the coronary arteries are unable to supply normal blood flow to the heart muscle due to surgical interventions such as aortic cross-clamping. In this circuit a portion of the patient's blood is withdrawn from the arterial side of the extracorporeal circuit (A-V loop), mixed with a known quantity of cardioplegic solution containing the desired concentration of protective drugs, and pumped via a roller pump through flexible plastic conduits to a cannula introduced into the aortic root and/or coronary vessels. A small heat exchanger is usually included within this circuit in order to properly control the temperature of the blood-cardioplegia solution being introduced into the heart's vascular supply. After passing through the coronary vascular bed of the heart the residual blood-cardioplegia enters the coronary sinus where it gains entrance to the right atrial chamber of the heart. This mixture is either aspirated into the venous return cannulae or passes through the cardiopulmonary vascular system and is evacuated from the left ventricle by the ventricular vent circuit described in circuit #3 above. In either event, the residual blood-cardioplegia is reintroduced into the patient's general circulation through one of these routes.

This invention has achieved significant improvements in mass transfer, integration of blood pumping into the oxygenator device and the marked reduction in size and operational volume of the system. Such benefits are highly desirable in applying such technology to current approaches to cardiopulmonary bypass support of the surgical patient. The small device size and minimal operational volumes of this invention also make it ideally adaptable to newer approaches termed "minimally invasive cardiac surgery" in which the CPB system should be miniaturized and placed as close to the patient as possible. Such localization of the system to the surgical field makes traditional perfusionist control/operation difficult at best.

3) Use of Apparatus with Adaptive Control System

The invention may optionally be employed with use of an adaptive or "smart control" system logically integrating patient physiologic data, device operational characteristics and preprogrammed clinical limits in order to provide real time, automated control of the principal portions of the cardiopulmonary bypass circuit. Such a control system could be thought of as analogous to the Pilot/Autopilot relationship in modern passenger aircraft, as a skilled clinician (perfusionist) will monitor, and intercede where necessary, to ensure proper support of the patient, but routine real time operation of the device will be facilitated by the "Smart Controller". A schematic block diagram of such a smart controller is set forth in FIG. 26.

4) Renal Dialysis

The mass and heat transfer and pump apparatus described above can also be adapted for use in renal dialysis. As noted above, for this application, the preferred material of the hollow fibers 48 would be a compound such as polysulfone or cellulose triacetate which is selectively fluid permeable. With such materials, the apparatus may remove waste materials such as urea and creatinine from a patient's blood as it passes through the apparatus before being subsequently returned to the patient.

As background, one skilled in the hemodialysis field will recognize that the apparatus of the present invention can be utilized as a component of a dialysis system much like existing hemodialysis devices. See, for example, U.S. Pat. No. 5,722,944 to Folden (1998) which provide a general description of the hemodialysis process, the disclosure of which is hereby incorporated by reference in its entirety.

The hemodialysis circuit removes blood from the patient and passes it through a specially designed filter that functions as an artificial kidney. The dialyzer separates waste products from the patient's blood such as urea and creatinine. This cleansed blood is then subsequently returned to the patient. A typical hemodialysis circuit contains a blood pump which propels the blood through the dialyzer unit. Simultaneously, a separate pump propels the dialysate through the dialyzer unit where the blood and dialysate are separated by a semipermeable membrane. This dialysate creates a solute concentration gradient to drive diffusion of the waste components across the membrane. As the cleansed blood exits the dialyzer, it passes through an air detector and then is returned to the patient.

The present invention can be used to replace at least the blood side of the hemodialysis circuit. The present invention would be modified to allow a liquid dialysate, rather than a gas such as oxygen, to pass down through the multilumen shaft, through the at least one spoke to the inlet plenum, and subsequently across the hollow fibers where mass exchange takes place. These modifications specifically relate to the resizing of the diameters of the passages in the shaft to accommodate the requisite fluid flow rate. Further, the inlet chamber 25 may be modified to permit elimination of the separate dialysate concentrate pump.

5) Liver Assist Device

The mass and heat transfer and pump apparatus described above can also be adapted for use as a liver-assist device. As noted above, for this application, the preferred material of the hollow fibers 48 would be a selectively fluid permeable compound such as cellulose acetate. These fibers are subsequently seeded with cells derived from human hepatocytes as described is U.S. Pat. No. 5,368,555 to Sussman et al. and U.S. Pat. No 3,883,393 to Knazek et al., the disclosures of which are hereby incorporated by reference. With such materials, the apparatus may perform liver specific functions such as gluconeogenesis, ammonia metabolism, and detoxification on a patient's blood as it passes through the apparatus before being subsequently returned to the patient.

It should be recognized that the apparatus of the present invention can be utilized as a component of a liver-assist system much like existing hemodialysis devices as described in U.S. Pat. No. 5,368,555 to Sussman et al. which provide a general description of a system which can provide liver specific biologic processes; Jauregui, H. O., Mullon, C., Press, P., Trenkler, D., Naik, S., Santangini, H., Muller, T. & Solomon, B. In vivo evaluation of a hollow fiber liver assist device. *Hepatol.* 21:460–469, 1995 and Rozga, J., et al., "A Bioartificial Liver to Treat Sever Acute Liver Failure," Annals of Surgery, Vol. 219, No. 5, pp. 538–546 (1994); Rozga, J., et al., "Development of a Bioartificial Liver: Properties and Function of a Hollow-Fiber Module Inoculated with Liver Cells", Hepatology, Vol. 17, No. 2, pp. 258–265 (1993); Takashi, M. et al., Successful Treatment of Diabetes with the Biohybrid Artificial Pancreas in Dogs, Transplantation, Vol. 51, No. 1, pp. 43–51 (1991); and Sullivan, S. J., et al., "Biohybrid Artificial Pancreas: Long-Term Implantation Studies in Diabetic Pancreatectomized Dogs", Science, Vol. 252, pp. 718–721 (1991).

While the present invention has been described herein, it is distinctly understood that the invention is not limited thereto but may be otherwise variously embodied in the scope of the following claims and any equivalent thereof All articles, patents, and documents discussed in this continuation-in-part are hereby incorporated by reference.

We claim:

1. A blood pump-oxygenator comprising:
   (a) a housing defining a blood flow path and having a venous blood inlet, an arterial blood outlet, an oxygen inlet and an oxygen outlet;
   (b) a double lumen shaft defining a gas inlet path and a gas outlet path; wherein the double lumen shaft gas inlet path is in fluid communication with the housing gas inlet and the double lumen shaft gas outlet is in fluid communication with the housing gas outlet; and
   (c) at least one distributor element past which blood may flow, mounted on the double lumen shaft, the at least one distributor element having:
      (i) an inner ring with a first face and a second face;
      (ii) an outer ring concentrically spaced with respect to the inner ring such that the inner ring and the outer ring define an oxygen supply plenum and an oxygen return plenum;
      (iii) a first hollow spoke in fluid communication with the oxygen inlet path and the oxygen supply plenum;
      (vi) a second hollow spoke in fluid communication with the oxygen outlet path and the oxygen return plenum; and
      (vii) a plurality of selectively fluid-permeable membrane elements extending across the distributor disk blood flow path, each of the selectively fluid-permeable membrane elements in fluid communication with the oxygen supply plenum and the oxygen return plenum; and wherein when blood flows through the housing flow path and oxygen flows through and diffuses across the plurality of selectively fluid-permeable membrane elements and when the at least one distributor element rotates about the at least one double lumen shaft oxygenation/decarbonation of blood and simultaneous pumping of blood occurs.

2. The blood pump-oxygenator of claim 1, wherein the plurality of selectively fluid-permeable membrane elements extend across a first side of the distributor element and a plurality of fluid impermeable membrane elements extend across a second side of the distributor element, the fluid impermeable membrane elements being coupled to a fluid supply such that a heat exchange fluid can flow through the impermeable membrane elements to maintain the temperature of the blood.

3. The blood pump-oxygenator of claim 2, wherein the double lumen shaft comprises a third and a fourth lumen, the third lumen being in fluid communication with the fluid impermeable membrane elements and defining an inlet path for the heat exchange fluid and the fourth lumen being in fluid communication with the fluid impermeable membrane and defining an outlet flow path for the heat exchange fluid.

4. The blood pump-oxygenator of claim 2, wherein the blood flows substantially perpendicular to the plurality of fluid impermeable membrane elements.

5. The blood pump-oxygenator of claim 1, further comprising a motor coupled to the shaft that provides power to rotate the shaft.

6. The blood pump-oxygenator of claim 5, wherein the shaft is rotatably mounted to the housing, such that the shaft can rotate in two directions to agitate the blood, and the motor can power the shaft to rotate in the two directions.

7. The blood pump-oxygenator of claim 1, further comprising a seal disposed between the housing and the shaft.

8. The blood pump-oxygenator of claim 1, wherein the fluid-permeable membrane elements comprise polyethylene.

9. The blood pump-oxygenator of claim 1, wherein the fluid-permeable membrane elements comprise polypropylene.

10. The blood pump-oxygenator of claim 1, wherein the fluid-permeable membrane elements are coupled to the distributor element with a potting material.

11. The blood pump-oxygenator of claim 1, wherein the plurality of selectively fluid-permeable elements comprise a first set of selectively fluid-permeable elements that extend in a first direction and parallel to each other across the at least one distributor element and a second set of selectively fluid-permeable elements that extend in a second direction and parallel to each other across the at least one distributor element.

12. The blood pump-oxygenator of claim 1, wherein the plurality of selectively fluid-permeable elements comprise a first set of selectively fluid-permeable elements that extend in a first direction across the at least one distributor element and a second set of selectively fluid-permeable elements that extend in a second direction across the at least one distributor element at a preferred angle to the first direction.

13. The blood pump-oxygenator of claim 1, wherein the first hollow spoke has a cross-sectional shape of an airfoil.

14. The blood pump-oxygenator of claim 1, wherein the oxygen supply plenum extends around about half of the at least one distributor element, and the oxygen return plenum extends around about the other half of the at least one distributor element.

15. A blood pump-oxygenator, comprising:
a housing defining an interior through which blood can flow;
a rotatable shaft, rotatably mounted within the housing, the shaft having a supply lumen through which a first fluid can flow;
a ring, disposed within the interior of the housing and mounted to the rotatable shaft, the ring comprising:
(i) a first side and a second side;
(ii) a plurality of hollow fibers that are fluid permeable and that extend across the first side of the ring;
(iii) a first annular lumen extending along an arc within the ring, the first annular lumen being in fluid communication with the supply lumen and the plurality of hollow fibers, such that as blood passes through the interior of the housing and the shaft and ring are rotated the blood is pumped through the housing and, the first fluid travels from the supply lumen, through the first annular lumen and to the plurality of hollow fibers and diffuses through the plurality of hollow fibers into the blood.

16. The blood pump-oxygenator of claim 15, further comprising a plurality of fluid impermeable membrane elements that extend across the second side of the ring, the fluid impermeable membrane elements being coupled to a fluid supply such that a heat exchange fluid can flow through the impermeable membrane elements to maintain the temperature of the blood.

17. The blood pump-oxygenator of claim 16, wherein the shaft comprises a third and a fourth lumen, the third lumen defining an inlet path for the heat exchange fluid and being in fluid communication with the fluid impermeable elements and the fourth lumen defining an outlet flow path for the heat exchange fluid and being in fluid communication with the fluid impermeable elements.

18. The blood pump-oxygenator of claim 16, wherein the blood flows substantially perpendicular to the plurality of fluid impermeable membrane elements.

19. The blood pump-oxygenator of claim 15, wherein the ring further comprises a first spoke, extending from the supply lumen to the annular lumen, that defines a first radial lumen and a second spoke, extending from the annular lumen to the discharge lumen, that defines a second radial lumen.

20. The blood pump-oxygenator of claim 19, wherein the first spoke has a cross-section that comprises an airfoil.

21. The blood pump-oxygenator of claim 15, further comprising a motor coupled to the shaft to drive the shaft and the ring to rotate and thereby pump blood through the blood pumpoxygenator.

22. The blood pump-oxygenator of claim 21, wherein the shaft is rotatably mounted to the housing, such that the shaft can rotate in two directions to agitate the blood, and the motor can power the shaft to rotate in the two directions.

23. The blood pump-oxygenator of claim 15, wherein the shaft further comprises a discharge lumen that runs substantially parallel to the supply lumen and wherein the first fluid travels through the supply lumen, through the first annular lumen and through the plurality of hollow fibers so that a gas exchange takes place between the blood and the first fluid to define a second fluid that passes through the discharge lumen.

24. The blood pump-oxygenator of claim 15, further comprising a plurality of rings that are each, disposed within the interior of the housing and rotatably mounted to the shaft, each of the plurality of rings comprising:
(i) a plurality of hollow fibers that are fluid permeable extending from the ring; and
(ii) a first annular lumen extending along an arc within the respective ring, the first annular lumen being in fluid communication with the supply lumen.

25. The blood pump-oxygenator of claim 15, wherein the plurality of hollow fibers comprise a plurality of fibers of polyethylene.

26. The blood pump-oxygenator of claim 15, wherein the plurality of hollow fibers comprise a plurality of fibers of polypropylene.

27. The blood pump-oxygenator of claim 15, wherein the plurality of hollow fibers are coupled to the ring with a potting material.

28. The blood pump-oxygenator of claim 15, wherein the plurality of hollow fiber comprise a first set of selectively fluid-permeable elements that extend in a first direction and parallel to each other across the ring and a second set of selectively fluid-permeable elements that extend in a second direction and parallel to each other across the ring.

29. The blood pump-oxygenator of claim 15, wherein the plurality of selectively fluid-permeable elements comprise a first set of selectively fluid-permeable elements that extend in a first direction across the ring and a second set of selectively fluid-permeable elements that extend in a second direction across the ring at a preferred angle to the first direction.

30. A blood pump-oxygenator, comprising:
- a housing defining an interior through which blood can flow;
- a shaft, rotatably mounted within the housing, the shaft having a first supply lumen through which a first fluid can flow, a second supply lumen through which a heat exchange fluid can flow, a third lumen that is in fluid communication with the first supply lumen and that defines an outlet path for the first fluid, and a fourth lumen that is in fluid communication with the second supply lumen and that defines an outlet path for the heat exchange fluid;
- a ring, disposed within the interior of the housing and mounted to the rotatable shaft, the ring comprising:
  (i) a first set of hollow fibers that are fluid permeable extending from the ring;
  (ii) a first annular lumen extending along an arc within the ring, the first annular lumen being in fluid communication with the first supply lumen and the third lumen, such that when blood passes through the interior of the housing and the ring is rotated, the first fluid flows from the first supply lumen to the first set of hollow fibers, diffuses through the first set of hollow fibers and into the blood such that a gas exchange takes place with the blood and the first fluid then flows through the third lumen; and
  (iii) a second set of hollow fibers that are fluid impermeable extending from the ring, the second set of hollow fibers being in fluid communication with the second supply lumen, such that heat exchange fluid can flow from the second supply lumen, through the second set of hollow fibers where heat transfer occurs between the blood and the heat exchange fluid and the second set of hollow fibers being in fluid communication with the fourth lumen, so that the heat exchange fluid can flow from the second set of hollow fibers to the fourth lumen.

31. The blood pump-oxygenator of claim 30, wherein the ring further comprises a first spoke, extending from the first supply lumen to the first annular lumen, to define a first radial lumen and a second spoke, extending from the first annular lumen to the third lumen, to define a second radial lumen.

32. The blood pump-oxygenator of claim 31, wherein the first spoke has a cross-section that comprises an airfoil.

33. The blood pump-oxygenator of claim 30, further comprising a motor coupled to the shaft to drive the shaft and the ring to rotate and thereby pump blood through the blood pump-oxygenator.

34. The blood pump-oxygenator of claim 33, wherein the shaft is rotatably mounted to the housing, such that the shaft can rotate in two directions, and the motor can power the shaft to rotate in the two directions.

35. The blood pump-oxygenator of claim 30, wherein the third lumen runs substantially parallel to the first supply lumen.

36. The blood pump-oxygenator of claim 30, further comprising a plurality of rings that are each, disposed within the interior of the housing and rotatably mounted to the shaft, each of the plurality of rings comprising:
  (i) a first set of hollow fibers that are fluid permeable extending from the ring; and
  (ii) a first annular lumen extending along an arc within the respective ring, the first annular lumen being in fluid communication with the first supply lumen.

37. The blood pump-oxygenator of claim 30, wherein the first set of hollow fibers comprise a plurality of fibers of polyethylene.

38. The blood pump-oxygenator of claim 30, wherein the first set of hollow fibers comprise a plurality of fibers of polypropylene.

39. The blood pump-oxygenator of claim 30, wherein the first set of hollow fibers are coupled to the ring with a potting material.

40. The blood pump-oxygenator of claim 30, wherein the first set of hollow fibers comprise a first group of selectively fluid-permeable elements that extend in a first direction and parallel to each other across the ring and a second group of selectively fluid-permeable elements that extend in a second direction and parallel to each other across the ring.

41. The blood pump-oxygenator of claim 30, wherein the first set of hollow fibers comprise a first group of selectively fluid-permeable elements that extend in a first direction across the ring and a second group of selectively fluid-permeable elements that extend in a second direction across the ring that is at a preferred angle to the first direction.

42. The blood pump-oxygenator of claim 30, wherein the blood flows substantially perpendicular to the second set of hollow fibers.

* * * * *